United States Patent
Wang et al.

(10) Patent No.: US 10,457,892 B2
(45) Date of Patent: Oct. 29, 2019

(54) FATTY ACID ESTER-BASED WAX COMPOSITIONS AND METHODS OF MAKING THEREOF

(71) Applicant: Iowa State University Research Foundation, Inc., Ames, IA (US)

(72) Inventors: Tong Wang, Ames, IA (US); Tao Fei, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/239,031

(22) Filed: Jan. 3, 2019

(65) Prior Publication Data

US 2019/0136149 A1    May 9, 2019

Related U.S. Application Data

(62) Division of application No. 15/875,803, filed on Jan. 19, 2018.

(Continued)

(51) Int. Cl.
   *C11C 3/00*             (2006.01)
   *C11C 5/00*             (2006.01)
   (Continued)

(52) U.S. Cl.
   CPC .............. *C11C 3/003* (2013.01); *C08L 91/06* (2013.01); *C11C 5/002* (2013.01); *A61K 8/922* (2013.01); *C11C 5/006* (2013.01)

(58) Field of Classification Search
   CPC .......... C11C 3/003; C11C 5/002; C08L 91/06; A61K 8/922
   See application file for complete search history.

(56) References Cited

U.S. PATENT DOCUMENTS 2,476,609 A * 7/1949 Lerner ................... C07C 41/60
                                                     554/168
2,783,161 A     2/1957 Padgett
(Continued)

FOREIGN PATENT DOCUMENTS

| DE | 241860 A1 | 1/1987 |
|---|---|---|
| GB | 468533 A | 7/1937 |
| KR | 20140074519 A | 6/2014 |

OTHER PUBLICATIONS

Fei, "Developing Soybean Oil-Based Coating and Binding Materials and Environmental Friendly Solvent System for Recovery of Poly-Beta-Hydroxybutyrate (PHB)," Thesis, Iowa State University, Ames, IA (Nov. 27, 2017).

(Continued)

*Primary Examiner* — Yate' K Cutliff
(74) *Attorney, Agent, or Firm* — Pepper Hamilton LLP

(57) ABSTRACT

This invention relates to a wax composition comprising one or more fatty acid diester compounds having the formula of

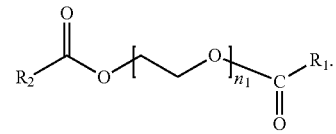

$R_1$ and $R_2$ are each independently a substituted or unsubstituted $C_4$ to $C_{50}$ alkyl or aryl; and $n_1$ is an integer from 2 to 10. This invention also relates to a wax composition comprising: a) one or more fatty acid monoester or diester compounds having the formula of:

(Continued)

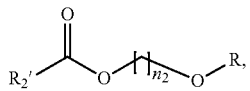

and b) one or more hydroxylated fatty acid diester compounds having the formula of

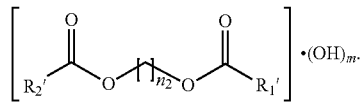

In these formulae, R is H or $COR_1'$; $R_1'$ and $R_2'$ are each independently a substituted or unsubstituted $C_4$ to $C_{50}$ alkyl or aryl; $n_2$ is an integer from 2 to 24; m is an integer from 2 to 12; and $.(OH)_m$ represents 2 to 12 hydroxyl groups substituting for 2 to 12 hydrogen atoms in the alkyl groups $R_1'$ and/or $R_2'$. Uses of the compositions are also disclosed.

11 Claims, 5 Drawing Sheets

Related U.S. Application Data

(60) Provisional application No. 62/448,760, filed on Jan. 20, 2017.

(51) Int. Cl.
   *C08L 91/06*      (2006.01)
   *A61K 8/92*       (2006.01)

(56) References Cited

U.S. PATENT DOCUMENTS

| | | |
|---|---|---|
| 3,129,104 A | 4/1964 | Callinan et al. |
| 3,857,805 A | 12/1974 | Prickril |
| 4,431,833 A | 2/1984 | Lodhi et al. |
| 5,434,278 A | 6/1995 | Pelloso et al. |
| 6,824,572 B2 | 11/2004 | Murphy |
| 7,510,584 B2 | 5/2009 | Cap |
| 8,147,606 B2 | 4/2012 | Heinrichs |

OTHER PUBLICATIONS

Fei et al., "Synthesis and Characterization of Soybean Oil-Based Waxes and Their Application as Paraffin Substitute for Corrugated Coating," Journal of Industrial and Engineering Chemistry 1-10 (2017).

Fei "Developing Vegetable Oil-Based Coating Materials," Presentation, Iowa State University Department of Food Science and Human Nutrition Seminar (Nov. 2, 2016).

Christie, "Triacylglycerols: Part I. Structure and Composition," Scottish Crop Research Institute (2011).

Seo et al., "PEGylation of Conjugated Linoleic Acid and Its Application as an Anti-Cancer Prodrug," Key Engineering Materials 342-343:441-444 (2007).

DD 241860, Wolf, J. et al., Cleaning of filters, English Abstract, 1 page (Year: 1987).

KR 20140074519, Lee, J., Aqueous Manicure Compositions, English translation, 17 pages (Year: 2014).

KR 20140074519, Lee, J., Aqueous Manicure Compositions, English Abstract, 3 pages (Year: 2014).

Wang et al., "Chemical Modification of Partially Hydrogenated Vegetable Oil to Improve its Functional Properties for Candles," J. Am. Oil Chem. Soc. 84(12):1149-1159 (2007).

* cited by examiner

FATTY ACID ESTER-BASED WAX COMPOSITIONS AND METHODS OF MAKING THEREOF

This application is a divisional of U.S. patent application Ser. No. 15/875,803, filed Jan. 19, 2018, which claims the benefit of U.S. Provisional Patent Application Ser. No. 62/448,760, filed Jan. 20, 2017, all of which are hereby incorporated by reference in their entirety.

FIELD OF THE INVENTION

The present invention relates to novel fatty acid ester based wax compositions and methods of making and using thereof.

BACKGROUND OF THE INVENTION

Paraffin is one of the most widely used waxes for making candles and as water-proofing agent for packaging and food industries. The use of paraffin is dictated by a combination of its desirable properties, including melting profile, hardness, cohesiveness, clarity, and heat stability. According to a study by The Freedonia Group, U.S. demand for waxes is to grow at a rate of 1.8% annually through 2019. However, because paraffin is a petroleum based product, it is not sustainable, nor recyclable or biodegradable. Due to the environmental issues caused by three billion pounds of paraffin-coated corrugated paper products being sent to landfills every year, the demand for a "green" material continues to increase. Many are seeking alternatives, and vegetable oil has been studied as a desirable potential raw material for the production of waxes having properties comparable to those of paraffin.

Paraffin is a mixture of saturated hydrocarbons that contain 80-90% linear chains with an average of 20-30 carbons (Palou et al., "Characterization of the Composition of Paraffin Waxes on Industrial Applications," *Energy Fuels* 28(2): 956-63 (2014)). The properties of refined paraffin depend on the proportion of the linear and chains in the hydrocarbons. A high concentration of branched chains leads to undesirable oily surface and can negatively affect physical properties such as hardness, friction resistance, melting point, consistency, and clarity (Palou et al., "Characterization of the Composition of Paraffin Waxes on Industrial Applications," *Energy Fuels* 28(2): 956-63 (2014)).

Vegetable oil-based waxes are typically obtained by modifying the composition or structures of fatty acids, such as partial or full hydrogenation, and interesterification, to achieve desired physical properties. Other chemical modifications are also used to attach functional groups on the acyl chain to achieve certain desirable properties. Several studies have reported that incorporating hydroxyl groups, branched chains, and short-chain fatty acids could improve the cohesiveness of vegetable oil-based waxes (Feuge et al., "Modification of Vegetable Oils. XII. Plasticity of Some Aceto Derivatives of Monostearin," *J. Am. Oil Chem. Soc.* 29:11-14 (1952); U.S. Pat. No. 5,434,278 to Pelloso et al.). However, very few studies systematically studied the structure-functionality relationships.

Despite the efforts made in these modifications to the composition or structures of fatty acids, vegetable oil-based waxes still are not widely used on a commercial scale, because of their limitations in delivering desired physical properties, e.g., they are either too hard and brittle or too soft and greasy, and have poor melting and recrystallization profiles. Fully hydrogenated soybean oil (FHSO) alone is not suitable for making candles or as coatings because of its brittle texture. Though introducing branched groups into the fatty acyl chain by epoxidation, ring opening, and esterification improved its cohesiveness, such materials had a significantly lower hardness and melting point compared to the commercial paraffin (Wang et al., "Chemical Modification of Partially Hydrogenated Vegetable Oil to Improve its Functional Properties for Candles," *J Am Oil Chem. Soc.* 84:1149-59 (2007)). Increasing the structure heterogeneity and the amount of hydroxyl groups or incorporating other functional groups, such as using partial acylglycerols, may also improve cohesiveness by interfering orderly packing and improving intermolecular interaction. For example, a study showed that incorporating acetyl and hydroxyl groups in FHSO improved its cohesiveness. However, hardness suffered in an acetylated FHSO. Also, the use of stearyl alcohol for deriving long-chain and linear esters could improve hardness, but it lowered cohesiveness (Yao et al., "Synthesis and Characterization of Acetylated and Stearylyzed Soy Wax," *J. Am. Oil Chem. Soc.* 90: 1063-71 (2013)). To date, no good biorenewable material to replace petroleum paraffin has been identified.

Therefore, there remains a strong need to obtain various biodegradable wax materials that can be derived from renewable raw materials, with a high melting point, high cohesiveness, high hardness, high clarity, good water repellency, and low coefficient of surface friction suitable to replace petroleum paraffin. The present invention is directed to fulfilling this need in the art.

SUMMARY OF THE INVENTION

One aspect of the invention relates to a wax composition comprising one or more fatty acid diester compounds having the formula of:

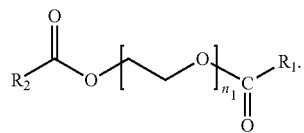

$R_1$ and $R_2$ are each independently a substituted or unsubstituted $C_4$ to $C_{50}$ alkyl or aryl; and $n_1$ is an integer from 2 to 10.

Another aspect of the invention relates to a wax composition comprising: a) one or more fatty acid monoester or diester compounds having the formula of:

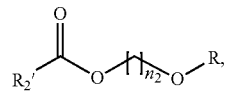

and b) one or more hydroxylated fatty acid diester compounds

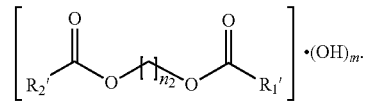

having the formula of:

Component a) and component b) are blended together in the wax composition. In these formulae, R is H or $COR_1'$; $R_1'$ and $R_2'$ are each independently a substituted or unsubstituted $C_4$ to $C_{50}$ alkyl or aryl; $n_2$ is an integer from 2 to 24; m is an integer from 2 to 12; and $.(OH)_m$ represents 2 to 12 hydroxyl groups substituting for 2 to 12 hydrogen atoms in the alkyl groups $R_1'$ and/or $R_2'$.

Another aspect of the invention relates to a process for preparing a wax composition. The process comprises providing one or more saturated free fatty acids having the formula of:

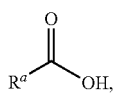

wherein $R^a$ is a substituted or unsubstituted $C_4$ to $C_{50}$ alkyl. Also provided is a polyethylene glycol having the formula of

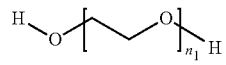

a diol having a formula of

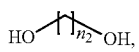

or mixture thereof, wherein $n_1$ is an integer from 2 to 10, and $n_2$ is an integer from 2 to 24. The polyethylene glycol, the diol, or mixture thereof is reacted with the one or more saturated free fatty acids in the presence of an esterification catalyst at a temperature of 60° C. to 120° C., thereby forming one or more fatty acid monoester or diester compounds. The esterification catalyst is then removed from the formed fatty acid monoester or diester compounds.

The present invention has established structure-function relationships for the modification of the lipid structure of fatty acid esters to deliver desirable physical properties of petroleum paraffin. Vegetable oil, such as soybean oil, was explored as a feedstock. Saturated free fatty acids (SFFA) derived from fully hydrogenated soybean oils (FHSO) were used to investigate the structure-function relationships. The inventors of the present application successfully developed various fatty acid esters or mixtures thereof derived from soybean oils, with a hardness, cohesiveness, water repellency, and melting profile comparable to those of paraffin wax.

In the present invention, the inventors of the present application discovered that an increase in the chain length significantly increased the hardness of the fatty acid esters. For instance, an increase in the chain length of the fatty acid ester from 18 carbon atoms to 34 carbon atoms significantly increased the hardness of the fatty acyl esters from 0.6 $mm^{-1}$ to 1.0 $mm^{-1}$, as the inverse of the penetration depth by a penetration test. Introduction of hydroxyl groups at the linear end of the fatty acid esters (e.g., forming a fatty acid monoester) further increased the hardness by promoting molecular alignments or chain lengthening via hydrogen bonding. For instance, incorporating hydroxyl groups at the linear end of the fatty acid ester chain increased the hardness to a value of 2.7 $mm^{-1}$. Pendent hydroxyl groups on the fatty acid esters greatly increased cohesiveness by improving intermolecular interactions, but can decrease the hardness of the fatty acid diesters. For instance, incorporating 0.5 wt % pendent hydroxyl group to the fatty acid esters greatly increased the cohesiveness of ethylene glycol mono/diesters from 145 to 1,325 g·mm, as the bending or breaking energy. Also, the cohesiveness of the fatty acid diesters can be significantly increased by introducing a C—O—C bond, but an excessive number of C—O—C bonds can negatively affect the hardness. For instance, using PEG to incorporate a C—O—C ether bond to the fatty acid ester, forming a PEG fatty acid diester (e.g., PEG200D), increased the cohesiveness to about 3,000 g·mm. Introducing an aromatic ring structure at the linear end of the fatty acid diesters can decrease the hardness, but the cohesiveness can be improved when hydrogen bond donors are present, because the aromatic ring structure served as a hydrogen bond acceptor, promoting the intermolecular hydrogen bonding with the hydrogen bond donors. For instance, the addition of aromatic ring structure (e.g., a phenyl group) at the linear end of the fatty acid diester chain decreased the hardness significantly from 2.8 to 0.9 $mm^{-1}$; however, the cohesiveness was improved from 310 to 712 g·mm, when hydrogen bond donors were present. These structure-function relationships demonstrate that the structure modifications to the fatty acid esters can result in various biorenewable wax materials to replace petroleum paraffin.

In the examples of the present application, various fatty acid monoesters, fatty acid diesters, and hydroxylated fatty acid esters were prepared and characterized. PEG200 fatty acid diester, a mixture of 0.5 wt % hydroxylated ethylene glycol fatty acid diester with ethylene glycol fatty acid monoester/diester, and a mixture of 1 wt % hydroxylated 1,16-hexadecanediol fatty acid diester with 1,16-hexadecanediol fatty acid diester provided very desirable physical properties for being used as paraffin substitute.

The inventors of the present application discovered that these fatty acid esters derived from vegetable oils are desirable wax coating alternatives that have coating performance competitive to that of paraffin. In particular, when hydrophobic particles (such as hydrophobic silica nanoparticles or microparticles) are mixed with these fatty acid esters, the resulting coating composition, when used to prepare a coated material (such as coated cardboard), can significantly improve the water resistance and wet strength of the coated materials.

BRIEF DESCRIPTION OF THE DRAWINGS

FIG. 1 shows the effect of chain length and hydroxyl groups at the linear end of the fatty acid esters on the hardness and cohesiveness of the fatty acid monoesters.

FIG. 2A shows the effect of incorporating various amounts of 1,16 DD-OH (1 wt % and 2 wt %) into 1,16 DD on the hardness and cohesiveness of the fatty acid diesters. FIG. 2B shows the effect of incorporating various amounts of EGD-OH (0.5 wt %, 1 wt %, and 2 wt %) into EGMD on the hardness and cohesiveness of the fatty acid esters.

FIG. 3 shows the effect of introducing C—O—C bonds into fatty acid diesters on the hardness and cohesiveness of the fatty acid diesters.

FIG. 4 shows the effect of introducing an aromatic ring structure on the hardness and cohesiveness of the fatty acid esters.

DETAILED DESCRIPTION OF THE INVENTION

Definitions

Figure 1:
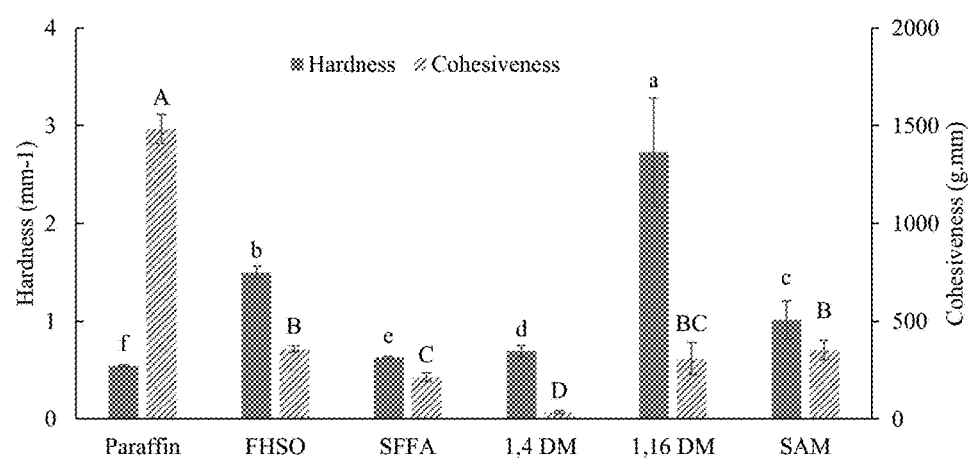
FIG. 1 compares the hardness and cohesiveness results of 1,4-butanediol fatty acid monoester (1,4 DM), 1,16-hexadecanediol fatty acid monoester (1,16 DM), and stearyl alcohol fatty acid monoester (SAM), against the hardness and cohesiveness of the reference paraffin, the fully hydrogenated soybean oil (FHSO) and saturated free fatty acids (SFFA).

As used herein, the following terms, unless otherwise indicated, shall be understood to have the following meanings. If not defined otherwise herein, all technical and scientific terms used herein have the same meaning as is commonly understood by one of ordinary skill in the art to which this invention belongs. In the event that there is a plurality of definitions for a term herein, those in this section prevail unless stated otherwise.

"Hydrocarbon radical" or "hydrocarbon group" typically consists only of carbon and hydrogen. The term used herein typically includes aliphatic hydrocarbon radicals (e.g., alkane, alkene or alkyne) may be of linear (unbranched), branched, or cyclic hydrocarbon structure, and saturated or unsaturated. Branched hydrocarbon means that one or more lower alkyl groups such as methyl, ethyl, or propyl are attached to a linear hydrocarbon chain.

The term "alkyl" refers to an aliphatic hydrocarbon group which may be a linear (unbranched), branched, or cyclic hydrocarbon structure or combination thereof. Representative alkyl groups are those having 28 or fewer carbon atoms. Branched alkyl means that one or more alkyl groups such as methyl, ethyl, or propyl are attached to a linear alkyl chain.

The statement that alkyl is intended to include linear, branched, or cyclic hydrocarbon structures and combinations thereof means that an "alkyl" group also includes the combinations of linear and cyclic structural elements.

The term "aryl" as used herein includes 5-, 6- and 7-membered single-ring aromatic groups that may include from zero to four heteroatoms. Examples include benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics."

The term "acyl" refers to an aliphatic hydrocarbon group of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl.

The term "fatty acid" generally refers to a carboxylic acid which bears a hydrocarbon radical. The hydrocarbon radical has been described above, and can have from about 4 to 50 carbon atoms in length. Typical fatty acids have 4 to 30 carbon atoms, 4 to 28 carbon atoms, 8 to 26 carbon atoms, 8 to 24 carbon atoms, 8 to 22 carbon atoms, 12 to 22 carbon atoms, 12 to 18 carbon atoms, 14 to 22 carbon atoms, or 15 to 18 carbon atoms. They may be of a natural or synthetic origin. Fatty acids can be saturated, unsaturated, or polyunsaturated. When they are unsaturated, they may contain one or more, for example two, three or more, double bonds.

The above terms "hydrocarbon radical", "alkyl", "aryl", and "fatty acid" may be optionally substituted, substituted or unsubstituted.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkenyl, haloalkenyl, cycloalkyl, cycloalkenyl, hydroxy, alkoxy, acyl, carboxy, carboalkoxy (also referred to as alkoxycarbonyl), carboxamido (also referred to as alkylaminocarbonyl), cyano, carbonyl, nitro, amino, alkylamino, dialkylamino, acylamino, amidino, mercapto, alkylthio, sulfoxide, sulfone, and/or sulfonic acid groups. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds. The terms "stable compound" or "stable structure" mean a compound that is sufficiently robust to survive isolation to a useful degree of purity from a reaction mixture, and formulation into an efficacious agent.

In the characterization of some of the substituents, certain substituents may combine to form rings. Unless stated otherwise, it is intended that such rings may exhibit various degrees of unsaturation (from fully saturated to fully unsaturated), may include heteroatoms, and may be substituted with other substituent groups as described above.

The compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration. Thus, a carbon-carbon double bond depicted arbitrarily herein as trans may be Z, E, or a mixture of the two in any proportion.

The Wax Composition

One aspect of the present invention relates to a wax composition comprising one or more fatty acid diester compounds having the formula of:

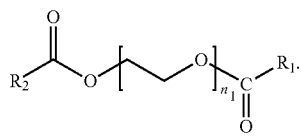

$R_1$ and $R_2$ are each independently a substituted or unsubstituted $C_4$ to $C_{50}$ alkyl or aryl; and $n_1$ is an integer from 2 to 10.

$R_1$ and $R_2$ may be the same or different, and are each independently a substituted or unsubstituted alkyl or aryl. For instance, $R_1$ and $R_2$ are each independently a substituted or unsubstituted $C_4$ to $C_{28}$ alkyl, a substituted or unsubstituted $C_8$ to $C_{22}$ alkyl, a substituted or unsubstituted $C_{14}$ to $C_{22}$ alkyl, or a substituted or unsubstituted $C_{15}$ to $C_{18}$ alkyl. Typically, $R_1$ and $R_2$ are each independently an unsubstituted alkyl. In some embodiments, one of $R_1$ and $R_2$ is aryl, such as phenyl or substituted phenyl.

The integer $n_1$ can range from 2 to 10, for instance, from 3 to 5. Typically, the moiety

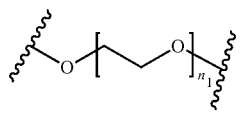

is derived from a polyethylene glycol having a molecular weight ranging from 100 to 400 g/mol, e.g., PEG200 (molecular weight of 200 g/mol) or PEG400 (molecular weight of 400 g/mol).

The wax composition may contain a single PEG fatty acid diester compound, or a mixture of two or more different PEG fatty acid diester compounds. Exemplary PEG fatty acid diesters (PEGD) are PEG200 fatty acid diester (PEG200D) and PEG400 fatty acid diester (PEG400D), as shown infra in Example 3.

The wax composition can have a melting point ranging from 55° C. to 80° C., for instance, from 60° C. to 75° C., from 65° C. to 75° C., or from 70° C. to 75° C.

The wax composition has a penetration hardness of 1.6 mm or below (i.e., a penetration distance), for instance, 1.5 mm or below, 1.4 mm or below, 1.3 mm or below, 1.2 mm or below, 1.1 mm or below, or 1.0 mm or below. The penetration hardness is measured by a standard needle penetration test according to the ASTM D1321 standard, with a 100 g cone and the penetration being conducted for 5 seconds at 23° C. The penetration hardness can also be characterized by an inverse conversion of the penetration distance, as illustrated infra in Example 5.

The wax composition has a cohesiveness of 1000 to 4500 g·mm, for instance, 1200 to 3500 g·mm, 1300 to 3100 g·mm, or 1500 to 3000 g·mm. The cohesiveness is measured by the energy required to bend or break a 4 mm-thick wax disk placed on a three-bar instrument, with two vertical support bars 12 mm apart and a third bar attached to the crosshead of the instrument being driven perpendicularly into the wax disk for 3 mm at a speed of 0.5 mm/s, as illustrated infra in Example 5.

Another aspect of the invention relates to a wax composition comprising:

a) one or more fatty acid monoester or diester compounds having the formula of:

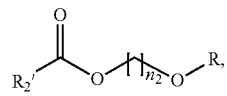

and b) one or more hydroxylated fatty acid diester compounds having the formula of:

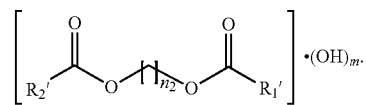

Component a) and component b) are blended together in the wax composition. In these formulae, R is H or $COR_1'$; $R_1'$ and $R_2'$ are each independently a substituted or unsubstituted $C_4$ to $C_{50}$ alkyl or aryl; $n_2$ is an integer from 2 to 24; m is an integer from 2 to 12; and $\cdot(OH)_m$ represents 2 to 12 hydroxyl groups substituting for 2 to 12 hydrogen atoms in the alkyl groups $R_1'$ and/or $R_2'$.

When R is H, the compound

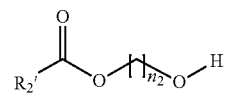

is a fatty acid monoester compound. When R is $COR_1'$, the compound

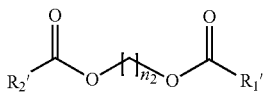

is a fatty acid diester compound.

$R_1'$ and $R_2'$ may be the same or different, and are each independently a substituted or unsubstituted alkyl or aryl. For instance, $R_1'$ and $R_2'$ are each independently a substituted or unsubstituted $C_4$ to $C_{28}$ alkyl, a substituted or unsubstituted $C_8$ to $C_{22}$ alkyl, a substituted or unsubstituted $C_{14}$ to $C_{22}$ alkyl, or a substituted or unsubstituted $C_{15}$ to $C_{18}$ alkyl. Typically, $R_1'$ and $R_2'$ are each independently an unsubstituted alkyl. In some embodiments, one of $R_1$ and $R_2$ is aryl, such as phenyl or substituted phenyl.

The integer $n_2$ can range from 2 to 24. Typically, the moiety

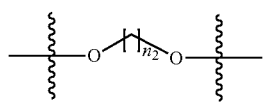

is derived from an aliphatic diols having a formula of

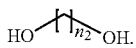

The exemplary aliphatic diols have been described infra.

In component b), the integer m can range from 2 to 12. The moiety $.(OH)_m$ therefore, represents 2 to 12 hydroxyl groups substituting for 2 to 12 hydrogen atoms in the alkyl groups $R_1'$ and/or $R_2'$. This typically means that two or more hydroxyl groups have been introduced to the fatty acid ester chain of the fatty acid diester compound

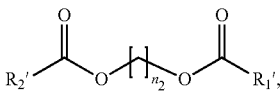

replacing two or more hydrogen atoms in the alkyl groups $R_1'$ and/or $R_2'$, forming the "hydroxylated" fatty acid diester compounds in component b).

Component a) may contain a diol fatty acid monoester compound, a diol fatty acid diester compound, or a mixture of a diol fatty acid monoester/diester compound.

Component b) may contain a single hydroxylated diol fatty acid diester compound, or a mixture of two or more different hydroxylated fatty acid diester compounds.

In certain embodiments, the wax composition can further comprise component c) blended with component a) and component b). The component c) comprises one or more fatty acid diester compounds having the formula of:

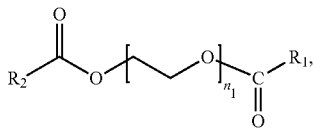

wherein $R_1$ and $R_2$ are each independently a substituted or unsubstituted $C_4$ to $C_{50}$ alkyl or aryl; and $n_1$ is an integer from 2 to 10. The component c) is the same PEG fatty acid diester compound as described, supra. All the embodiments described, supra, regarding this PEG fatty acid diester compound are suitable as the component c).

Typically, when the wax composition contains a PEG/diol fatty acid ester compound having an aryl group as the ester group (i.e., any of the $R_1$, $R_2$, $R_1'$, and $R_2'$ variables in the above formulae is an aryl), the wax composition also includes a PEG/diol fatty acid monoester compound, so that the hydroxyl group at the linear end of the PEG/diol fatty acid monoester (i.e., the hydroxyl group that is not esterified) can serve as a hydrogen bond donor interacting with the aryl group.

In some embodiments, the wax composition comprises component a) and component b) blended together, in which the component a) is an ethylene glycol saturated fatty acid monoester and/or diester, and the component b) is a hydroxylated ethylene glycol fatty acid diester. For instance, the wax composition contains a blend of ethylene glycol saturated fatty acid monoester/diester mixture (EGMD) and hydroxylated ethylene glycol fatty acid diester (EGD-OH).

In some embodiments, the wax composition comprises component a) and component b) blended together, in which the component a) is an ethylene glycol saturated fatty acid monoester and/or diester, and the component b) is a hydroxylated 1,16-diol fatty acid diester.

In some embodiments, the wax composition comprises component a) and component b) blended together, in which the component a) is a 1,16-diol saturated fatty acid monoester and/or diester, and the component b) is a hydroxylated 1,16-diol fatty acid diester. For instance, the wax composition contains a blend of 1,16 diol saturated fatty acid monoester/diester mixture (1,16 DMD) and hydroxylated 1,16 fatty acid diester (1,16 DD-OH).

In the wax composition containing a blend of component a) and component b), the component a) can range from 50 wt % to 99 wt % of the wax composition, for instance, from 75 wt % to 99 wt %, from 85 wt % to 99 wt %, or from 90 wt % to 95 wt % of the wax composition. The component b) can range from 1 wt % to 50 wt % of the wax composition, for instance, from 1 wt % to 25 wt %, from 1 wt % to 15 wt %, or from 5 wt % to 10 wt % of the wax composition. When the concentration of the component b) is too high, the wax composition may become too soft or become a liquid at ambient temperature, which may be undesirable for its application as wax.

Alternatively, the concentration of the component b) can be represented based on the percentage pendent —OH groups in the wax composition, which can range from 0.05 wt % to 20 wt % of the wax composition, for instance, from 0.1 wt % to 10 wt %, from 0.5 wt % to 5 wt %, or from 0.5 wt % to 2 wt % of the wax composition.

The wax composition can have a melting point ranging from 55° C. to 80° C., for instance, from 60° C. to 75° C., from 65° C. to 75° C., or from 70° C. to 75° C.

The wax composition has a penetration hardness of 1.6 mm or below (i.e., a penetration distance), for instance, 1.5 mm or below, 1.4 mm or below, 1.3 mm or below, 1.2 mm or below, 1.1 mm or below, or 1.0 mm or below. The penetration hardness is measured by a standard needle penetration test according to the ASTM D1321 standard, with a 100 g cone and the penetration being conducted for 5 seconds at 23° C. The penetration hardness can also be characterized by an inverse conversion of the penetration distance, as illustrated infra in Example 5.

The wax composition has a cohesiveness of 500 to 3000 g·mm, for instance, 800 to 3000 g·mm, 800 to 2500 g·mm, 1000 to 2000 g·mm, 1200 to 1800 g·mm, or 1300 to 1500 g·mm. The cohesiveness is measured by the energy required to bend or break a 4 mm-thick wax disk placed on a three-bar instrument, with two vertical support bars 12 mm apart and a third bar attached to the crosshead of the instrument being driven perpendicularly into the wax disk for 3 mm at a speed of 0.5 mm/s, as illustrated infra in Example 5.

As exemplified in the examples, the wax composition of the present invention based on the fatty acid esters possesses very desirable physical properties and can replace petroleum paraffin.

Additionally, the wax composition of the present invention presents properties of a wax more desirable than petroleum paraffin. For instance, the wax composition of the present invention, like many waxes, is saponifiable, i.e., it can be hydrolyzed under basic conditions into water-soluble components. On the other hand, paraffin, although often referred to as paraffin wax, is not saponifiable.

Preparation of the Wax Composition

Another aspect of the invention relates to a process for preparing a wax composition. The process comprises providing one or more saturated free fatty acids having the formula of:

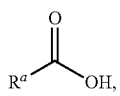

wherein $R^a$ is a substituted or unsubstituted $C_4$ to $C_{50}$ alkyl. Also provided is a polyethylene glycol having the formula of

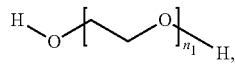

a diol having a formula of

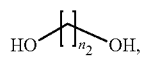

or mixture thereof, wherein $n_1$ is an integer from 2 to 10, and $n_2$ is an integer from 2 to 24. The polyethylene glycol, the diol, or mixture thereof is reacted with the one or more saturated free fatty acids in the presence of an esterification catalyst at a temperature of 60° C. to 120° C., thereby forming one or more fatty acid monoester or diester compounds. The esterification catalyst is then removed from the formed fatty acid monoester or diester compounds.

The fatty acids used in this invention are saturated free fatty acids. The term "fatty acid" has been described herein. Typically, the saturated free fatty acid used herein has the formula of:

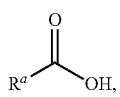

wherein $R^a$ is a substituted or unsubstituted $C_4$ to $C_{50}$ alkyl. For instance, $R^a$ is a substituted or unsubstituted $C_4$ to $C_{28}$ alkyl, a substituted or unsubstituted $C_8$ to $C_{26}$ alkyl, a substituted or unsubstituted $C_8$ to $C_{22}$ alkyl, a substituted or unsubstituted $C_{14}$ to $C_{22}$ alkyl, or a substituted or unsubstituted $C_{15}$ to $C_{18}$ alkyl. Typically, $R^a$ is an unsubstituted alkyl.

The saturated free fatty acids may be derived from a natural or synthetic fatty acid. The saturated free fatty acids herein can vary depending on the source of fatty acids used. Exemplary fatty acid sources include butyric acid, caproic acid, caprylic acid, capric acid, decenoic acid, lauric acid, cis-9-dodecenoic acid, myristic acid, myristoleic acid, cis-9-tetradecenoic acid, pentadecanoic acid, palmitic acid, palmitoleic acid, cis-9-hexadecenoic acid, heptadecanoic acid, heptadecenoic acid, stearic acid, oleic acid, linoleic acid, linolenic acid, α-linolenic acid ricinoleic acid, dihydroxystearic acid, nonadecanoic acid, arachidic acid, cis-9 acid, cis-11-eicosenoic acid, eicosadienoic acid, eicosatrienoic acid, arachidonic acid, eicosapentaenoic acid, behenic acid, erucic acid, docosadienoic acid, 4,8,12,15,19-docosapentaenoic acid, docosahexaenoic acid, lignoceric acid, tetracosenoic acid, and mixtures thereof. Any of the above fatty acids can be fully hydrogenated to prepare the saturated free fatty acids.

Additionally, suitable saturated free fatty acids or mixture thereof can also be obtained from fully hydrogenated fats or vegetable oil, by methods known to one skilled in the art. For instance, saturated free fatty acids used in this invention can be produced from fully hydrogenated vegetable oils via a saponification process followed by an acidification process as described in Ferdous et al., "Preparation and Optimization of Biodiesel Production from Mixed Feed Stock Oil," Chemical Engineering and Science 1(4): 62-66 (2011), which is hereby incorporated by reference in its entirety, and optionally with minor modifications. The major components in most vegetable oils are triacylglycerols (TAGs). The physical properties of TAGs depend on the length of the fatty acyl chains, the amount and type of unsaturation in the fatty acid chains, and the distribution of fatty acyl groups among the sn-positions of the TAGs (U.S. Pat. No. 6,824,572 to Murphy, which is hereby incorporated by reference in its entirety). Exemplary fully hydrogenated fats or vegetable oils are fully hydrogenated soybean oil, fully hydrogenated cottonseed oil, fully hydrogenated sunflower oil, fully hydrogenated canola oil, fully hydrogenated corn oil, fully hydrogenated palm oil, fully hydrogenated olive oil, fully hydrogenated peanut oil, fully hydrogenated safflower oil, fully hydrogenated coconut oil, fully hydrogenated rapeseed oil, fully hydrogenated castor oil, fully hydrogenated mustard seed oil, fully hydrogenated tallow oil, fully hydrogenated bone oil, fully hydrogenated fish oil, fully hydrogenated tall oil, or mixtures thereof. These hydrogenated fats or vegetable oils are readily commercially available. Alternatively, hydrogenated fats or vegetable oils can be made by processes known in the art. Typically, the fatty acids used herein are a mixture of saturated free fatty acids prepared from fully hydrogenated soybean oil.

The polyethylene glycol (PEG) used herein may be commercially available, or prepared by methods known to one skilled in the art. Typical polyethylene glycol used has a molecular weight of less than 10,000 g/mol, less than 5,000, less than 1,000, less than 500, or ranging from 100 to 400 g/mol. Suitable polyethylene glycol has a formula of:

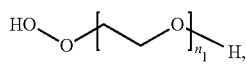

wherein $n_1$ is an integer from 2 to 10, for instance, from 3 to 5. Exemplary polyethylene glycols are PEG200 (molecular weight of 200 g/mol) and PEG400 (molecular weight of 400 g/mol).

The diols used herein are aliphatic diols having a formula of

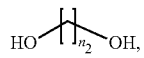

in which $n_2$ is an integer from 2 to 24. Exemplary diols are ethylene glycol, 1,3-propanediol, 1,4-butanediol, 1,5-pentanediol, 1,6-hexanediol, 1,8-octanediol, 1,10-decanediol, 1,12-dodecanediol, 1,13-tridecanediol, 1,16-hexadecanediol, 1,18-octadecanediol, 1,19-nonadecanediol, 1,20-icosanediol, 1,22-docosanediol, and 1,24-tetracosanediol. The diols may be commercially available, or prepared by methods known to one skilled in the art.

To prepare the wax compositions of the present invention, one or more saturated free fatty acids are esterified with an above-described polyethylene glycol, a diol, or mixture thereof.

The esterification reaction is typically carried out in the presence of an esterification catalyst. In principle, any acidic, nonvolatile esterification catalyst can be used in the esterification reaction. Typically, the esterification catalyst is solid acidic catalyst, such as a strong acidic ion exchange resin containing the residues of strong acids in their free form bound to a polymer matrix. As recognized by those skilled in the art, ion exchange resins of the type are commercially available from a variety of sources in various forms, e.g., as small beads, and under various names, for instance, an Amberlyst® 15 catalyst. Typically, the esterification catalyst is present in a concentration ranging from 0.1 to 10 wt % of the total reactants, for instance, from 0.5 to 5 wt % of the total reactants, or from 2 to 5 wt % of the total reactants.

The esterification reaction can be carried out over a wide range of temperatures. Typically, the reaction is carried out at a temperature no higher than 120° C., for instance, at a temperature ranging from 60 to 120° C., from 70 to 100° C., or from 80 to 95° C.

The duration of the esterification reaction can be over a broad range of times. Typically, an almost complete conversion of saturated free fatty acid to the corresponding fatty acid esters can be achieved in 12 hours or less.

The saturated free fatty acid used in the esterification is typically but not limited to an equal molar amount or an excess molar amount than the PEG, diol, or mixture thereof. Thus, the PEG, diol, or mixture thereof to the saturated free fatty acid molar ratio is equal to or less than 1. The molar ratio of the PEG, the diol, or mixture thereof to the saturated free fatty acid depends on the desirable amount of fatty acid monoesters in the fatty acid ester product. When the molar ratio of the PEG, the diol, or mixture thereof to the saturated free fatty acid is equals to or less than 1:2, the product contains mainly fatty acid diesters. When the molar ratio of the PEG, the diol, or mixture thereof to the saturated free fatty acid is equal to or less than 1 but greater than 1:2, the product contains a mixture of fatty acid monoester/diester. The product can contain mainly fatty acid monoesters when the molar ratio of the PEG, the diol, or mixture thereof to the saturated free fatty acid is about 1 or greater. Typically, the molar ratio of the PEG, the diol, or mixture thereof to the one or more saturated free fatty acid typically ranges from 1.5:1 to 1:3, for instance, from 1:1 to 1:1.5, from 1:1 to 1:1.2, from 1:1 to 1:1.1, or from 1.5:1 to 1:1.

When the starting material for the esterification reaction contains a PEG, the resulting fatty acid ester can contain a PEG fatty acid monoester and/or PEG fatty acid diester compound. When the PEG to the saturated free fatty acid molar ratio is 1:2, the reaction produces mainly a PEG fatty acid diester compound having the formula of:

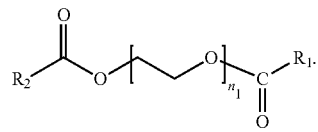

The variables $R_1$, $R_2$, and $n_1$ are the same as described, supra.

When the starting material for the esterification reaction contains a diol, the resulting fatty acid ester can contain a diol fatty acid monoester and/or a diol fatty acid diester compound having the formula of:

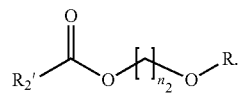

The variables R, $R_1'$, $R_2'$, and $n_2$ are the same as described, supra.

When the starting material for the esterification reaction contains one or more different saturated free fatty acids, it can result in a fatty acid diester compound having two different ester groups, i.e., $R_1$ and $R_2$ in the above PEG fatty acid diester formula may be different, and $R_1'$ and $R_2'$ in the above diol fatty acid diester formula may be different.

Also, when the starting material for the esterification reaction contains one or more different saturated free fatty acids, the resulting wax composition can contain a mixture of different fatty acid ester compounds, with the ester groups resulting from different fatty acids. This is the case when the saturated free fatty acid is obtained from fully hydrogenated fats or vegetable oil, because these fats or vegetable oils typically contain a mixture of triglycerides having a variety of fatty acid residues. For example, a typical fatty acid composition in soybean oil is as shown in Table 1 below.

TABLE 1

A Typical Fatty Acid Composition in Soybean Oil

| Fatty acid | Weight Percent[1] |
|---|---|
| Palmitic acid | 10.5 |
| Stearic acid | 4.5 |
| Oleic acid | 23.0 |
| Linoleic acid | 53.0 |
| Linolenic acid | 7.5 |
| Other | 1.5 |

[1]Weight percent of total fatty acid mixture derived from hydrolysis of soybean oil.

To append an aryl group as one of the ester groups to the PEG fatty acid ester or the diol fatty acid ester compound (e.g., any of $R_1$, $R_2$, $R_1'$, and $R_2'$ in the above formulae is aryl), a PEG fatty acid monoester or a diol fatty acid monoester may be prepared. The hydroxyl group on the PEG fatty acid monoester or the diol fatty acid monoester is then reacted with an aromatic carboxylate compound, under reaction conditions similar to the esterification reaction described, supra. Alternatively, a transesterification reaction between a PEG fatty acid diester or a diol fatty acid diester and an aromatic hydroxy compound may be carried out to attach an aryl group as one of the ester groups to the PEG fatty acid ester or the diol fatty acid ester compound. Exemplary aryl groups include phenyl and substituted phenyl.

After the esterification reaction is completed, the esterification catalyst is removed from the formed fatty acid monoester or diester compounds. The catalyst may be removed by any method known to one skilled in the art, such as filtration (e.g., hot filtration), or precipitation.

Alternatively, the esterification process can start with a hydroxylated free fatty acid. The process then comprises providing a hydroxylated free fatty acid having the formula of $(OH)_{m'}$.

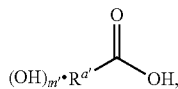

wherein $R^{a'}$ is a substituted or unsubstituted $C_4$ to $C_{50}$ alkyl, m' is an integer from 1 to 6, and $(OH)_{m'}$ represents 1 to 6 hydroxyl groups substituting for 1 to 6 hydrogen atoms in the alkyl group $R^{a'}$. Also provided is a polyethylene glycol having the formula of:

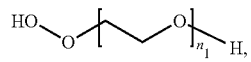

a diol having a formula of

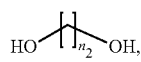

or mixture thereof, wherein $n_1$ is an integer from 2 to 10, and $n_2$ is an integer from 2 to 24. The polyethylene glycol, the diol, or mixture thereof is reacted with the hydroxylated free fatty acids in the presence of an esterification catalyst at a temperature of 60° C. to 120° C., thereby forming one or more hydroxylated fatty acid diester compounds. The esterification catalyst is then removed from the formed hydroxylated fatty acid diester compounds.

The process may also comprise the step of preparing the hydroxylated free fatty acid, by introducing one or more hydroxyl groups to the fatty acid ester chain via methods known to one skilled in the art. For instance, the process may start with preparing an expoxidized free fatty acid from expoxidization of an unsaturated free fatty acid, using a method described in Park et al., "Synthesis and Thermal Properties of Epoxidized Vegetable Oil," *Macromol Rapid Commun.* 25:724-27 (2004), which is incorporated herein by reference in its entirety, and optionally with minor modifications. The hydroxylated free fatty acid can then be produced by oxidizing-hydrolyzing the epoxidized free fatty acid, i.e., a water-promoted ring opening reaction, using a method described in Chen et al., "Polyols and Polyurethanes Prepared from Epoxidized Soybean Oil Ring-Opened by Polyhydroxy Fatty Acids with Varying OH Numbers," *J. Appl. Polym. Sci.* (2014), which is incorporated herein by reference in its entirety, with minor modifications.

All the embodiments described, supra, regarding the saturated free fatty acids, PEG, diol, esterification catalyst, the molar ratio of the reactants, and the esterification reaction conditions are suitable in this esterification process that starts with the hydroxylated free fatty acid.

Typically, the molar ratio of the PEG, the diol, or mixture thereof to the one or more hydroxylated free fatty acids typically ranges from 1:1 to 1:3, for instance, from 1:1 to 1:2, from 1:1 to 1.5, from 1:1 to 1.2, or from 1:1 to 1:1.1.

The process of preparing the wax composition of the present invention may also comprise the step of blending one or more of the above-formed PEG/diol fatty acid monoester or diester compounds with one or more of the above-formed hydroxylated fatty acid diester compounds.

Alternatively, when preparing a mixture of the component a), component b), and/or component c) described, supra, a PEG/diol or mixture thereof can be reacted with a mixture of a saturated free fatty acid and a hydroxylated fatty acid directly, in a one-pot reaction. This is exemplified in Example 3 infra.

In some exemplary embodiments, polyethylene glycol is provided to react with one or more saturated free fatty acids to obtain a PEG fatty acid ester wax composition (PD-wax). The PEG fatty acid ester can be a PEG fatty acid monoester or diester compound, depending on the ratio of the PEG to the saturated free fatty acid in the esterification reaction. PD-wax contains mainly a polyethylene glycol (PEG) diester of saturated fatty acids, and is prepared by a one-step esterification reaction as discussed above.

As an example, a PEG having an average molecular weight of 100-400 is mixed with a saturated free fatty acid, obtained from fully hydrogenated soybean oil, at a molar ratio of 1:2, in the presence of an Amberlyst® 15 catalyst (e.g., 5 wt %), and reacted at a temperature of 90° C. for 8 hours with continuous stirring. The reaction mixture is then subjected to hot filtration to remove the solid catalyst, and the resulting PEG fatty acid diester product is solidified and collected. An exemplary reaction scheme is shown below in Scheme 1.

Scheme 1. Reaction of PEG with a Saturated Free Fatty Acid to Prepare PEG Fatty Acid Diester (PEGD)

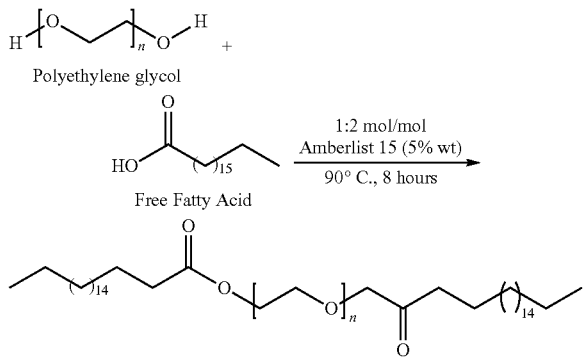

In some exemplary embodiments, a diol is provided to react with one or more saturated free fatty acids to obtain a diol fatty acid ester wax composition. The diol fatty acid ester can be a diol fatty acid monoester or diester compound, depending on the ratio of the diol to the saturated free fatty acid in the esterification reaction.

As an example, a diol (e.g., 1,16-hexadecanediol, or ethyleneglycol) is mixed with a saturated free fatty acid, obtained from fully hydrogenated soybean oil, at a molar ratio of 1:1.5, in the presence of an Amberlyst® 15 catalyst (e.g., 5 wt %), and reacted at a temperature of 90° C. for 12 hours with continuous stirring. The reaction mixture is then subjected to hot filtration to remove the solid catalyst, and the resulting diol fatty acid monoester/diester product is solidified and collected. Exemplary reaction schemes are shown below in Schemes 2 and 3.

Scheme 2. Reaction of 1,16-exadecanediol (1,16-diol) with a Saturated Free Fatty Acid to Prepare 1,16 Diol Fatty Acid Monoester/Diester (1,16 DMD).

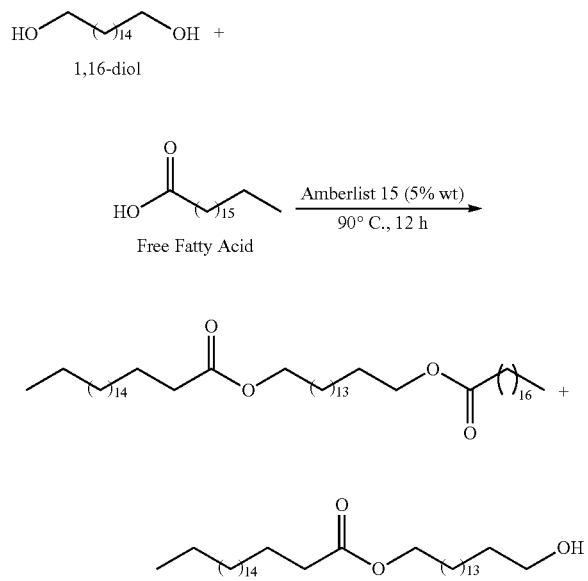

Scheme 3. Reaction of Ethylene Glycol with a Saturated Free Fatty Acid to Prepare Ethylene Glycol Fatty Acid Monoester/Diester (EGMD).

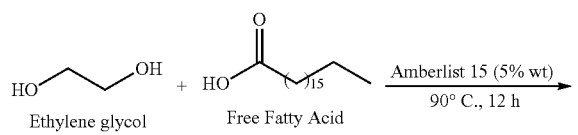

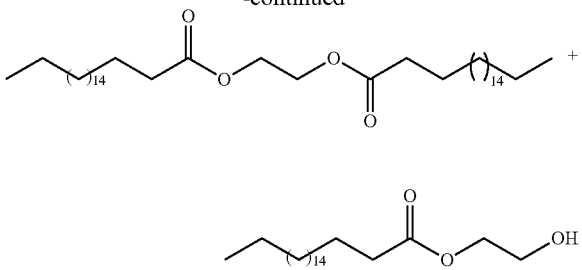

In some exemplary embodiments, the process is used to prepare a wax composition containing a mixture of fatty acid monoester, fatty acid diester, and hydroxylated fatty acid diester (MD-wax). Polyethylene glycol or a diol is provided to react with one or more saturated free fatty acids to obtain a PEG/diol fatty acid ester compound. Polyethylene glycol or a diol is also provided to react with one or more hydroxylated fatty acid to obtain a hydroxylated fatty acid ester compound. The PEG/diol fatty acid ester compound and the hydroxylated fatty acid ester compound are then blended in an appropriate ratio to provide desirable hardness and cohesiveness.

As an example, a diol fatty acid monoester/diester product is prepared according to the exemplary reaction schemes shown above in Schemes 2 and 3. Then, a diol (e.g., 1,16-hexadecanediol, or ethylene glycol) is mixed with a hydroxylated fatty acid, obtained from water-promoted ring opening of an epoxidized oleic acid, at a molar ratio of 1:2, in the presence of an Amberlyst® 15 catalyst (e.g., 5 wt %), and reacted at a temperature of 90° C. for 12 hours with continuous stirring, resulting in a hydroxylated fatty acid diester. An exemplary reaction scheme is shown below in Scheme 4. The diol fatty acid monoester/diester and the hydroxylated fatty acid diester are blended in an appropriate ratio to form a MD-wax composition. For instance, one exemplary MD-wax composition contains a blend of 90 wt % 1,16 diol fatty acid monoester/diester (1,16 DMD) and 10 wt % hydroxylated 1,16 fatty acid diester. Another exemplary MD-wax composition contains a blend of 95 wt % ethylene glycol fatty acid monoester/diester (EGMD) and 5 wt % hydroxylated ethylene glycol fatty acid diester (EGD-OH).

Scheme 4. Reaction of Ethylene Glycol (upper) or 1,16-hexadecanediol (1,16-diol)(lower) with a Hydroxylated Fatty Acid to Prepare Hydroxylated Fatty Acid Diester EGD-OH (upper) and 1,16 DD-OH (lower).

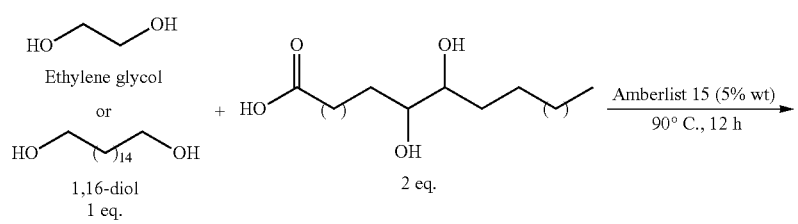

-continued

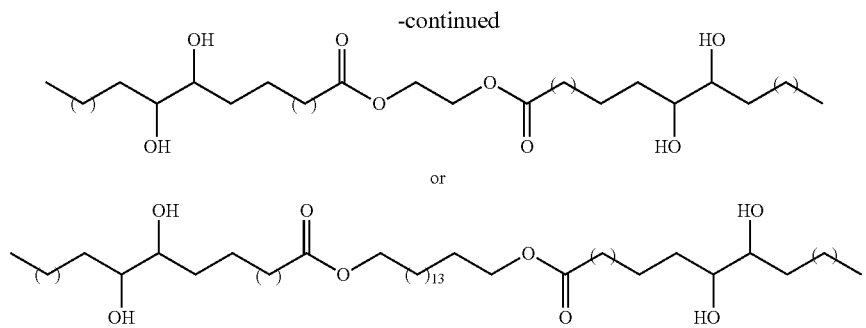

or

Use of the Wax Composition

The wax compositions of the present invention can be employed as pure substances or can be mixed with other wax components known to one skilled in the art, such as paraffin wax or beeswax, polyethylene waxes, polypropylene waxes, amide waxes, Fischer-Tropsch waxes, and the like.

The wax compositions described herein can be used to provide candles having a melting point that imparts desirable molding and/or burning characteristics. The candle comprises the wax compositions described supra and a candle wick.

Candles can be produced from the wax compositions described herein using various methods known to one skilled in the art. For instance, the wax composition can be heated to a molten state and then solidified around a wick (e.g., the molten material can be poured into a mold which includes a wick disposed therein, and then cooled to solidify in the shape of the mold). An exemplary description about molding of candles can be found in U.S. Pat. Nos. 6,019,804 and 8,529,924, which are hereby incorporated by reference in their entirety.

A wide variety of coloring agents and scenting agents, well known in the art of candle making, can be added to the wax composition, using methods known to one skilled in the art. For instance, a list of coloring agents containing one or more dyes or pigments and a list of scenting agents containing one or more perfumes, fragrances, essences or other aromatic oils, and the methods of incorporating these coloring agents and scenting agents into candles have been described in U.S. Pat. No. 8,529,924, which is hereby incorporated by reference in its entirety.

The wax compositions can be dissolved in solvents at an elevated temperature and be precipitated via cooling. Pastes thus prepared can be used in print applications for control of viscosity and of slip behavior.

The wax compositions of the present invention can be used as a coating composition. The wax composition comprised of the fatty acid esters described supra are desirable wax coating alternatives that have coating performance competitive to that of paraffin.

In one embodiment, the wax composition further comprises a hydrophobic particle. When these hydrophobic particles are mixed with the fatty acid esters of the present invention, the resulting coating composition, when used to prepare a coated material (such as coated cardboard), can significantly improve the water resistance and wet strength of the coated materials. This is because the hydrophobic particles may interact with the fatty acid esters or physically block the surface pore of the wax, thereby improving the water resistance and wet strength of the coated materials.

Suitable hydrophobic particles include carbon nanoparticles, metal or coated metal or metal oxide particles, mineral particles, silicate or doped silicate particles, silica particles, and polymer particles. The particles may themselves be hydrophobic (e.g., particles comprising PTFE), or the particles may be hydrophobized, in a manner known to one skilled in the art, to result in hydrophobic particles. For instance, typical hydrophobized treatments include the treatment of the particles with at least one compound selected from the group consisting of the alkyl silanes, fluoroalkylsilanes, perfluoroalkylsilanes, paraffins, waxes, fatty esters, functionalized long-chain alkane derivatives, disilazanes, and alkyl disilazanes. Particularly suitable hydrophobic particles are silica, clay, titania, ZnO, etc.

The hydrophobic particle can be a nanoparticle or a microparticle, with a size ranging from about 1 nm to about 500 μm. For instance, the size of the hydrophobic nanoparticle typically ranges from about 10 to about 500 nm, from about 10 to about 100, or from about 10 to about 50 nm; the size of the hydrophobic microparticle typically ranges from about 1 to about 100 μm, from about 1 to about 50 μm, or from about 10 to about 50 μm.

In one embodiment, the hydrophobic particles used in the wax composition for coating materials are hydrophobic silica nanoparticles or microparticles.

The hydrophobic particles may be present in the wax composition in a amount ranging from about 0.1 to about 30 wt %, from about 1 to about 20 wt %, from about 5 to about 15 wt %, or from about 1 to about 10 wt %.

When the wax composition of the present invention is used as a coating composition to coat a substitute, such as paper or cardboard, the washability of the wax-coated substrate, i.e., the amount of the wax washable or recoverable from the surface of the substrate, when treated with hot water, is much higher than the paraffin-coated substrate. This can lead to a high repulpability and recyclability of the coated material when the substrate is coated with the wax composition of the present invention.

Accordingly, the wax compositions of the present invention can be used to prepare a coated material. The coated material comprises the wax composition described supra and a substrate. The liquid or melted wax composition is used to encase the substrate.

Any method for packaging a wax material which results in wax-coated material having a finite size and shape using a film to surround the substrate is in general suitable. For example, three common techniques for adding a wax to a substrate (e.g., a corrugated board), i.e., curtain coating, wax cascading, and wax impregnation, can be used herein. In the curtain coating method, the wax composition with a melting temperature of about 75-80° C. is blended with other packaging compositions to create a blend that reduces the wax fracturing on the score lines of the corrugated board. The wax cascading method uses the wax composition with a melting temperature of about 60° C., with the corrugated sheets placed vertically as they pass through a waterfall of a molten wax. The wax impregnation method applies the wax composition to a corrugated board on a corrugator.

The coated material may also be prepared in a manner analogous to the methods for packaged hot melt adhesives as described in WO 02/061009, WO 04/037671, and U.S. Pat. Nos. 6,230,890, 5,806,285, 5,401,455, 5,715,654, and 4,039,485, which are hereby incorporated by reference in their entirety.

A wide variety of substrates (such as packaging substrates), well known in the art of package making, can be used in preparing the coated materials. For instance, a paper, a cardboard, or a thermoplastic polymer composition.

Suitable thermoplastic polymer composition include, but are not limited to, polypropylene, polyethylene and copolymers thereof, terpolymers of ethylene and ethylene/vinyl acetate, ethylene acrylate, ethylene methacrylate, ethylene methyl acrylate, ethylene methyl methacrylate, copolymers of ethylene and 1,6-mono- or di-unsaturated monomers, polyamides, polybutadiene rubber, polyesters such as polyethylene terephthatate, polybutylene terephthalate, polycarbonates, atactic poly-alpha-olefins, including atactic polypropylene, thermoplastic polyacrylamides, polyacrylonitrile, copolymers of acrylonitrile and other monomers such as butadiene, styrene, polymethyl pentene, polyphenylene sulfide, aromatic polyurethanes; styrene-acrylonitrile, acrylonitrile-butadiene-styrene, styrene-butadiene rubbers, acrylonitrile-butadiene-styrene elastomers. Suitable thermoplastic polymer compositions also include block copolymers comprising a polyvinyl aromatic block and a rubbery midblock which can be partly hydrogenated. The thermoplastic polymer composition may form a continuous film, a woven material, or non-woven material.

The wax composition of the invention can also be used in agricultural products, e.g., in fertilizer production and formulation. The wax composition of the invention may be used for time-released coatings, moisture- and water-barrier coatings, dust and fines control coatings, and inert carriers for ingredients. For instance, the wax composition of the invention may be formulated in a manner that provides a hard, non-cracking, water resistant fertilizer coating that breaks down over time, allowing for the controlled release of plant nutrients.

Accordingly, some embodiments of the present invention provide a biodegradable coating comprising the wax composition described supra and an emulsifier.

Any method for applying the biodegradable coating to the agricultural products is in general suitable. For instance, the biodegradable coating can be applied to the surface of a plant by rubbing the biodegradable coating onto the surface of the plant (e.g., by using of rubber gloves), by dipping or immersing the plant in the biodegradable coating, by spraying the biodegradable coating onto the plant, pouring the biodegradable coating onto the plant (e.g., when the plant is moving on a conveyor belt).

A wide variety of emulsifiers, well known in the art of food or plant coatings, can be used in preparing the packaging materials. In certain embodiments, the emulsifier is an edible emulsifier selected from non-ionic emulsifier, anionic emulsifier, and mixtures thereof. In some embodiments, the emulsifier enables the wax composition to be in a liquid form at room temperature. The emulsifier may facilitate the solubility of the wax composition in the coating. The emulsifier may serve as a pH modifier of the coating. Nonlimiting examples of suitable emulsifiers include morpholine, ammonia, lecithin, ethylene glycol monostearate, ammonium lauryl sulfate, sodium steroyl-2-lactylate, potassium oleate, propylene glycol monostearate, sodium alkyl sulfate, polyglycol, polyoxyethylene (20) sorbitan monooleate, and derivatives thereof.

The biodegradable coating based on the wax composition of the present invention has an antimicrobial effect on microorganisms, particularly food-borne pathogenic microorganisms, such as *Salmonella* and *Listeria monocytogenes*. As shown in the examples, the exemplary wax composition of the invention can destroy or inhibit the growth of microorganisms, particularly food-borne pathogenic microorganisms, by at least 10%, at least 20%, at least 30%, at least 40%, at least 50%, at least 60%, at least 70%, at least 80%, at least 90%, at least 95%, at least 99%, or virtually 100%.

The concentration of the wax composition in the biodegradable coating is typically at least 0.001 mg/mL to possess a desirable antimicrobial effect, for instance, at least 0.01 mg/mL, at least 0.05 mg/mL, at least 1 mg/mL, at least 5 mg/mL, at least 10 mg/mL, or at least 15 mg/mL.

Accordingly, the biodegradable coating is particularly suitable for usage as a coating for packaging such as food packaging.

EXAMPLES

The following examples are for illustrative purposes only and are not intended to limit, in any way, the scope of the present invention.

Example 1—Experimental Materials

Fully hydrogenated soybean oil (FHSO) was provided by Stratas Food (Memphis, Tenn.). Paraffin was provided by Michelman Inc. (Cincinnati, Ohio). Epoxidized oleic acid (EOA) and hydroxylated free fatty acid (HFFA) were produced by the methods described in Example 2. Polyethylene glycols (PEG) and other chemicals were purchased from Fisher Scientific (Pittsburgh, Pa.) and Sigma Aldrich (St. Louis, Mo.).

Example 2—Preparation of Epoxidized Oleic Acid, Hydroxylated Free Fatty Acid, and Saturated Free Fatty Acid Epoxidized oleic acid (EOA) was prepared for a ring opening reaction following a method reported by Park et al., "Synthesis and Thermal Properties of Epoxidized Vegetable Oil," *Macromol Rapid Commun.* 25:724-27 (2004), which is incorporated herein by reference in its entirety, with minor modifications. Briefly, oleic acid (56.4 g, 0.2 mol), glacial acetic acid (24.0 g, 0.4 mol), and a catalyst, Amberlyst-15 (5 g), were mixed in a round-bottom three-neck flask connected to a reflux condenser. The mixture was stirred by a mechanical stirrer and heated to 55° C., then 30% aqueous $H_2O_2$ (60 ml, 0.6 mol) was added dropwise. The reaction was allowed to remain at 55° C. for 7 hours. After the reaction, the catalyst was removed by filtration and the product was washed with hot distilled water until the pH was approximately 7.0.

Hydroxylated free fatty acid (HFFA) was produced by water-promoted ring opening of EOA using a method reported by Chen et al., "Polyols and Polyurethanes Prepared from Epoxidized Soybean Oil Ring-Opened by Polyhydroxy Fatty Acids with Varying OH Numbers," *J. Appl. Polym. Sci.* (2014), which is incorporated herein by reference in its entirety, with minor modification. Briefly, about 30 g EOA was mixed with deionized water (the molar ratio of the epoxy group of EOA to the hydroxyl group of water was 1:10) in a round-bottom flask with the presence of 0.1 wt % tetrafluoroboric acid as the catalyst. The reaction was carried out at 95° C. for 8 hours, and then the mixture was cooled to room temperature. The crude products were extracted with ethyl acetate and washed with saturated sodium chloride solution three times. Organic solvent was then removed at 80° C. using a roto-evaporator.

Saturated free fatty acid (SFFA) was produced from FHSO by a modified, saponification process followed by an acidification process (Ferdous et al., "Preparation and Optimization of Biodiesel Production from Mixed Feed Stock Oil," *Chemical Engineering and Science* 1(4): 62-66 (2011), which is hereby incorporated by reference in its entirety). FHSO was mixed with aqueous sodium hydroxide solution (4 M) at a molar ratio of 1:3 (oil: sodium hydroxide). The mixture was heated at 100° C. for 1 hour under reflux with vigorous mixing to form a soap solution. Hydrochloric acid was added at a molar ratio of 1:1.5 (soap: HCl) to acidify the soap solution. The mixture was heated at 100° C. for 1 hour and then cooled to room temperature. Saturated FFA was collected upon solidification and then dried in vacuum oven.

Example 3—Syntheses of Fatty Acyl Monoesters and Diesters with Alcohols/Diols of Different Chain Length and Functional Groups To produce monoesters of fatty acid with different alcohols, SFFA was mixed with 1,4-butanediol, 1,16-hexadecanediol, and stearyl alcohol, respectively, at a molar ratio of 1:1 in a round-bottom flask with 5 wt % of Amberlyst-15 as the catalyst. In each reaction, the mixture was heated at 95° C. in an oil bath for 12 hours. Hot filtration was used to remove the catalyst after the reaction. The collected liquid was cooled and saved in tin cans for $^1$H-NMR and textural analysis. Fatty acid monoesters, 1,4-butanediol fatty acid monoester (1,4 DM), 1,16-hexadecanediol fatty acid monoester (1,16 DM), and stearyl alcohol fatty acid monoester (SAM) were obtained. Those monoesters having reactive hydroxyl groups at the end of their linear chains provided functional groups for further esterification.

To attach a benzene ring to the fatty acid ester structure, 1,16 DM obtained above was mixed with benzoic acid at a molar ratio of 1:1, and the mixture was heated at 95° C. for 12 hours with 5 wt % Amberlyst-15 as the catalyst. Hot filtration was used to remove the catalyst after the reaction. The collected material was saved for further analysis. 1,16-hexadecanediol fatty acid and benzene diester (1,16 DD-R) was obtained.

To produce diesters of fatty acid with different alcohols, SFFA was esterified with 1,16-hexadecanediol, ethylene glycol, and PEG (molecular weight at 200 g/mol or 400 g/mol) at a molar ratio of 2:1, using the same reaction procedures and conditions as those discussed above for synthesizing fatty acid monoesters in this example. Fatty acid diesters, 1,16-hexadecanediol fatty acid diester (1,16 DD), ethylene glycol fatty acid diester (EGD), and PEG fatty acid diester (PEGD) were obtained.

To produce fatty acid diesters with pendent hydroxyl groups, HFFA was used to react with 1,16-hexadecanediol and ethylene glycol at a molar ratio of 2:1. The reaction procedures and conditions were the same as those discussed above for synthesizing fatty acid monoesters in this example. Hydroxylated fatty acid diesters (i.e., fatty acid diesters with pendent hydroxyl groups), hydroxylated 1,16-hexadecanediol fatty acid diester (1,16 DD-OH) and hydroxylated ethylene glycol fatty acid diester (EGD-OH) were obtained.

A mixture of ethylene glycol fatty acid monoester and fatty acid diester (EGMD) was also synthesized by using a SFFA to ethylene glycol mixing ratio of 1:0.75.

For evaluating the effect of pendent hydroxyl groups, 1,16 DD-OH and EGD-OH were separately mixed with 1,16 DD and EGMD, respectively, to form a mixture containing 0.5 wt %, 1 wt %, or 2 wt % of pendent —OH. The mixtures were then used to prepare samples for measuring the hardness and cohesiveness. To optimize and simplify the process, a mixture of EGD-OH and EGMD was synthesized in a one-pot reaction, instead of mixing individual components, i.e., a mixture of SFFA (95 wt %) and HFFA (5 wt %) was reacted with ethylene glycol at a molar ratio of 1:0.75. The materials used in subsequent coating performance tests in Examples 6 and 8 were all generated using such one-pot reaction.

Three synthesis replicates were done for each reaction.

Example 4—Determination of Structure and Purity of Esters $^1$H-NMR spectra of the products from each reaction in Example 3 were collected at room temperature using a Bruker AVIII-600 (Rheinstetten, Germany), and the proportion of monoester and diester formed was determined. Data was processed by using the MestReNova software (Mastrelab Research, Escondido, Calif., USA). All samples were prepared in chloroform-d (CDCl$_3$), and characterized as follows: stearyl alcohol fatty acid monoester (SAM): δ=2.3 ppm (2H, ), δ=4.3 ppm (2H, –

);

1,4 butanediol fatty acid monoester (1,4 DM): δ=2.3 ppm (2H,

),

δ=3.3 (2H, HO—CH$_2$—), δ=4.3 ppm (2H,

);

1,16-hexadecanediol fatty acid monoester (1,16 DM): same as 1,4 DM; 1,16-hexadecanediol fatty acid diester (1,16 DD): δ=2.3 (4H,

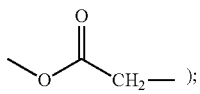

δ=4.3 (4H,

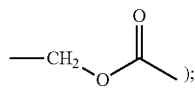

1,16-hexadecanediol fatty acid and benzene diester (1,16 DD-R): δ=2.3 (2H,

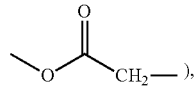

δ=4.2 (2H,

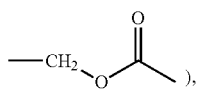

δ=7.5-8.0 (5H, H on benzene ring); ethylene glycol fatty acid diester (EGD): δ=2.3 (4H,

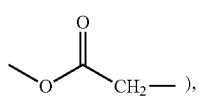

δ=4.5 (4H, —O—$CH_2$—$CH_2$—O—); polyethylene glycol 200 fatty acid diester (PEG200D): δ=2.3 (4H,

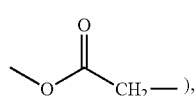

δ=3.6 (12H, —O—$CH_2$—$CH_2$—O—); EGD, and 1,16 DD with pendent hydroxyl groups: δ=2.3 (4H,

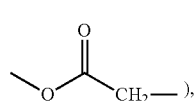

δ=3.6 (4H,

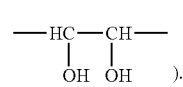

).

Example 5—Textural and Thermal Analyses of the Products

The changes in physical properties of the waxes such as hardness and cohesiveness were monitored for the samples produced in Examples 1-4. Paraffin was used as the reference for comparison.

Hardness was measured by using a Universal Penetrometer following the standard method of ASTM D1321. The distance that the standard needle penetrated into the wax sample (22 mm diameter, 15 mm height) was considered as the hardness after an inverse conversion (so that the higher the value, the harder the material is). Cohesiveness of the waxes were measured by using a TA-XTplus texture analyzer (Stable Micro Systems, Godalming, UK) according to the method reported by Yao et al., "Synthesis and Characterization of Acetylated and Stearylyzed Soy Wax," J. Am. Oil Chem. Soc. 90: 1063-71 (2013), which is hereby incorporated by reference in its entirety, with modifications. A three-point bend test using TA-92N was applied to measure the cohesiveness. A wax disk with a thickness of 4 mm was placed on two vertical support bars 12 mm apart. A third bar attached to the crosshead of the instrument was driven perpendicularly into the sample for 3 mm at a speed of 0.5 mm/s. The area under the curve of force-distance, which represents the energy required to bend or break the disc, was recorded as the cohesiveness.

The waxes having the hardness and cohesiveness comparable to that of paraffin were selected for further physical property analysis.

Coefficient of friction was measured by using a TA-265A sled fixture following ASTM standard method D1894. A standard weight (about 145 g) was placed on a surface uniformly coated with the wax, and the weight was pulled for 95 mm. The coefficient of friction was calculated by using the software Exponent (Hamilton, Mass.). Briefly, the maximum peak force, which was the force required to initiate motion, was recorded and the static coefficient of friction, s, was calculated as follows: s=As/B, wherein As=maximum force reading (g); and B=sled weight (g). The force used during uniform sliding was also recorded and the kinetic coefficient of friction, f was calculated as follows: f=Af/B, wherein Af=mean force reading obtained during uniform sliding (g); and B=sled weight (g).

Surface hydrophobicity of the waxes was measured by using a contact angle goniometer (Rame-Hart, Model 250; Succasunna, N.J.) to evaluate water repellency of the products. Wax samples with a thickness of about 2 mm were prepared using a weighing dish. A water droplet was applied on the surface (the bottom surface that formed in the dish) of the sample, and then the water contact angle was measured at 3 minutes.

Thermal analysis was performed on selected samples. Melting profiles of the waxes were determined by using a differential scanning calorimeter (DSC-7; Perkin-Elmer, Norwalk, Conn.) equipped with an Intracooling II system. About 8 mg of solid wax was weighed in a steel pan (Perkin-Elmer), and the pan was sealed. A blank steel pan was used as a reference. The temperature program started with 1-minute holding period at 20° C., followed by a 20° C./minute heating phase to 120° C., and a 3-minute holding period at 120° C. The sample was then cooled to 20° C. at a 20° C./minute rate. The peak point was taken as the melting point.

Example 6—Coating Performance Tests of the Selected Wax

The wax synthesized in Examples 1-4 which had similar hardness, cohesiveness, and melting points as those of paraffin were selected for simulated coating performance tests.

To prepare coated cardboard samples, non-coated cardboard was cut into approximately 50 mm×50 mm pieces and dipped into molten waxes for 5 seconds, and excessive wax was allowed to drip off the cardboard. The pieces were left to set for 3 hours at ambient temperature. The wax adsorption rate was calculated relative to the original cardboard weight.

Strength of the coated pieces was evaluated by using a bending test. The cardboard samples were placed on two vertical support bars which were 14 mm apart, and a blade attached to the crosshead of the instrument was driven perpendicular into the sample at a speed of 1 mm/second, with 10 mm of travel distance. The peak bending force was considered as the cardboard strength. To test water resistance of the coated cardboard, samples were soaked in ice water for 4 days, and the effect of soaking on the cardboard strength was measured by applying the same bending test.

Repulpability of the selected waxes was evaluated following the standard repulpability test procedure (the Corrugated Packaging Alliance, 2010) with minor modifications. Coated cardboard samples were cut into about 32 mm×102 mm strips and 25 g of the cardboard was placed in 1,500 mL hot water (52±5° C.) in a one-gallon Waring blender. The system was then blended at a low speed for 4 minutes, and then at a high speed for 5 minutes to de-flake the cardboard. All fine fibers were rinsed off the blender by running on a 0.01-inch-opening flat screen with 1-inch water head for 20 minutes. The accepted part ("accepts") (i.e., the portion that went through the screen) and the rejected part ("rejects") (i.e., the portion that retained on the screen) were collected and saved in aluminum weighing pans for drying at 105° C. for 12 hours. The percentage of the rejects was calculated by the following equation:

$$\% \text{ of Rejects} = \frac{\text{Net Rejects} \times 100}{\text{Net Accepts} + \text{Net Rejects}}$$

The waxes are considered repulpable if the percent of the rejects is less than 15%, and two out of three tests must pass this requirement.

Example 7—Statistical Analysis

In each of the examples presented here, three batches of waxes were synthesized for each treatment, and each synthesis batch provided one sample for measurements. The treatment effects were examined at the 5% significance level using Statistical Analysis System (SAS) 9.1 (SAS Institute, Cary, N.C.). The means and standard deviations were determined and presented.

Discussion of Examples 1-7
Structure Confirmation of the Synthesized Soybean Oil-Based Waxes 1H-NMR was used to monitor various reactions, as shown in Schemes 5-12, and to determine the structure and purity of the esters produced. It was confirmed that all reactions listed below were producing the expected monoesters and diesters, and all 8 reactions had conversion rate of above 90%.

The reactions details are shown in Schemes 5-12 below:

Scheme 5. Stearyl Alcohol Monoester (SAM), 95% Conversion (yield)

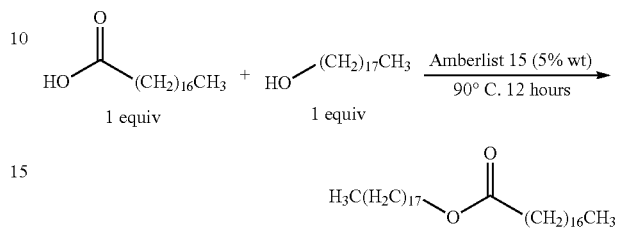

Scheme 6. 1,4-butanediol Fatty Acid Monoester (1,4 DM), 93% Conversion (yield)

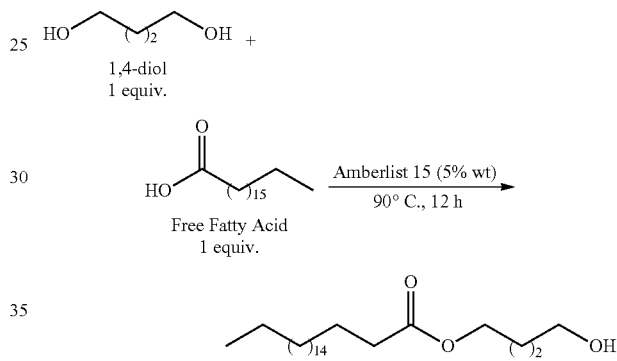

Scheme 7. 1,16-hexadecanediol Fatty Acid Monoester (1,16 DM), 95% Conversion (yield)

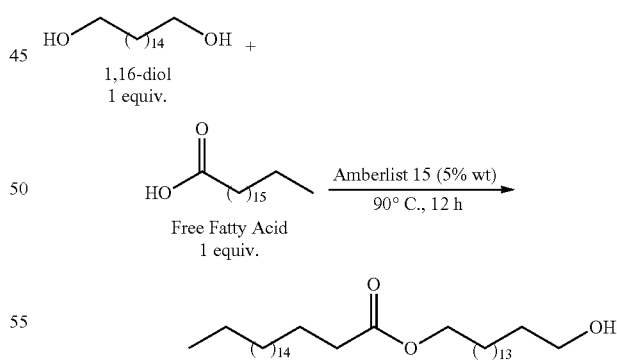

Scheme 8. 1,16-hexadecanediol Fatty Acid Diester (1,16 DD), 95% Conversion (yield)

-continued

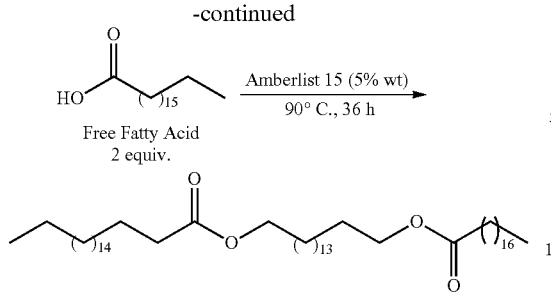

Free Fatty Acid
2 equiv.

Scheme 9. 1,16-hexadecanediol Fatty Acid and Benzene Diester (1,16 DD-R), 95% Conversion (yield)

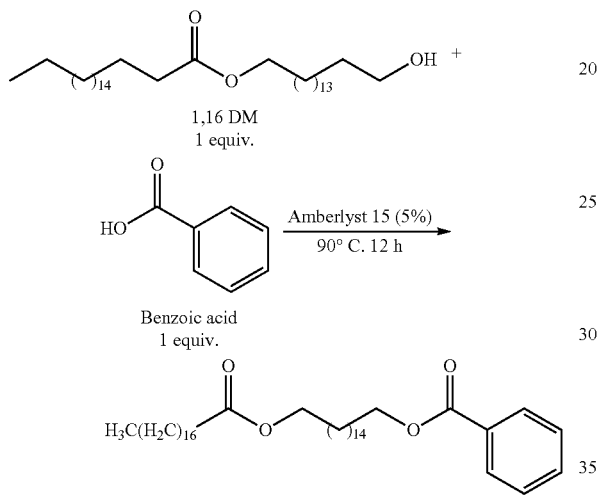

1,16 DM
1 equiv.

Benzoic acid
1 equiv.

Scheme 10. Ethylene Glycol Fatty Acid Diester (EGD), 95% Conversion (yield)

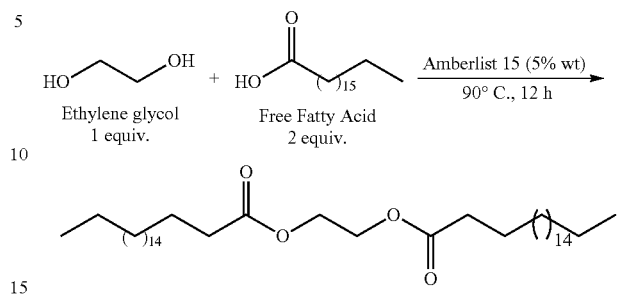

Ethylene glycol
1 equiv.

Free Fatty Acid
2 equiv.

Scheme 11. Polyethylene Glycol Fatty Acid Diester (PEGD), 93% Conversion (yield)

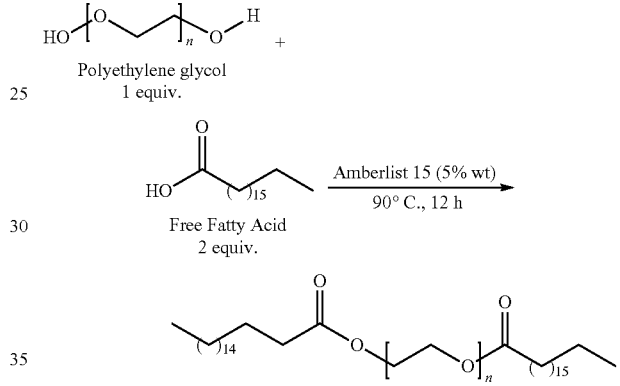

Polyethylene glycol
1 equiv.

Free Fatty Acid
2 equiv.

Scheme 12. Ethylene Glycol Fatty Acid Diester and 1,16-hexadecanediol Fatty Acid Diesters with Pendent Hydroxyl Group (EGD-OH and 1,16 DD-OH), 90% and 91% Conversion (yield), respectively

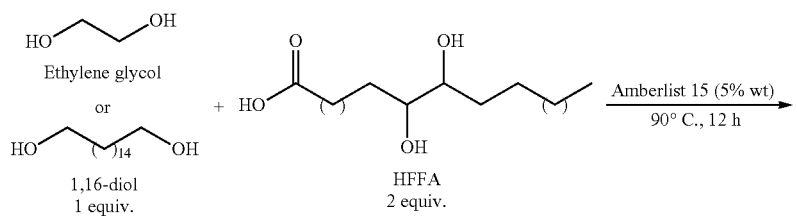

Ethylene glycol
or
1,16-diol
1 equiv.

HFFA
2 equiv.

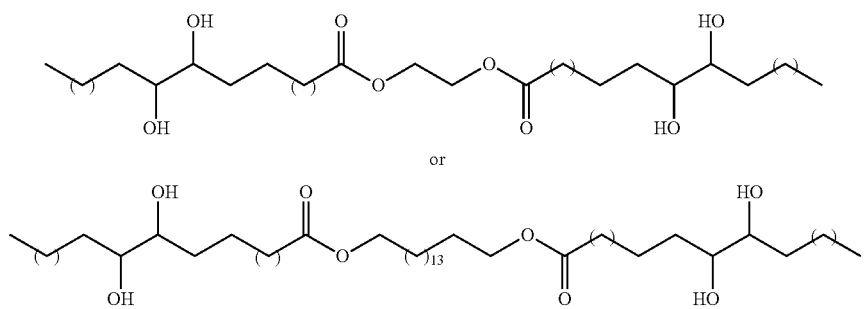

Impact of Chain Length of Alcohol/Diol and Functional Groups on the Hardness and Cohesiveness of Fatty Acid Monoesters Hardness and cohesiveness of different fatty acid monoesters were measured and compared to those of the starting materials as well as the reference paraffin wax. FIG. 1 shows that using 1,16-hexadecanediol and stearyl alcohol significantly increased the hardness of the fatty acid monoester produced (1,16 DM and SAM) compared to that of the SFFA, which indicates that an increase of the chain length will significantly increase the hardness. FIG. 1 also shows that 1,16 DM had a significantly higher hardness than that of SAM, which indicates that the hydroxyl group at the end of the linear chain further increases the hardness. This is likely achieved by an intermolecular alignment or a chain lengthening via hydrogen bonding. When linear molecules crystallize, the hydrogen bonding between the hydroxyl groups at the end of the linear chain further increases the apparent chain length and encourages more orderly and rigid packing. This observation agrees with the findings in carnauba wax, in which the long-chain hydroxyl acid esters were attributed for its high hardness (U.S. Pat. No. 3,129,104 to Callinan et al., which is hereby incorporated by reference in its entirety). However, use of a short chain di-alcohol, such as 1,4-butanediol, resulted a monoester (1,4 DM) with a hardness similar to that of SFFA, though a hydroxyl group was also incorporated at the end of the linear chain to enhance hydrogen bonding. Commercial paraffin, SFFA, SAM, 1,4 DM, FHSO, and 1,16 DM have apparent chain lengths of 20-30, 36, 36, 44, 54, and 68 carbon atoms, respectively. Corresponding to their respective chain lengths, paraffin, SFFA (having H-bonding between two carboxyl groups), SAM, and 1,4 DM had similar hardness, while FHSO (having 3 L crystalline arrangement) and 1,16 DM had higher hardness. These results indicate that improvement of the hardness can be primarily achieved by a significant increase of a carbon chain length.

The cohesiveness of the monoesters was also affected by the chain length and functional groups. The longer chain monoesters tended to be more cohesive. This is probably due to their higher hardness which also contributes to the resistance to bending. Overall, the monoesters synthesized did not appear to have a cohesiveness value comparable to that of paraffin, and no significant improvement in cohesiveness was observed when compared to that of the FHSO.

Impact of Pendent Hydroxyl Group and C—O—C Bond on the Hardness and Cohesiveness of the Fatty Acid Diesters Diesters with or without pendent hydroxyl group were produced using the HFFA and SFFA, respectively. The initial design was to compare the hardness and cohesiveness of each pure diester to evaluate the effect of pendent hydroxyl group on the hardness and cohesiveness. However, the diesters with pendent hydroxyl groups were either in a liquid form at ambient temperature, or were too soft to form a sample for a valid measurement of hardness and cohesiveness. Therefore, these diesters with pendent hydroxyl group were mixed with the high-melting-point monoesters or diesters to form a solid sample, in order to measure the effect of the pendent hydroxyl group on the modification of the physical properties of corresponding monoesters or diesters.

Figure 2A:
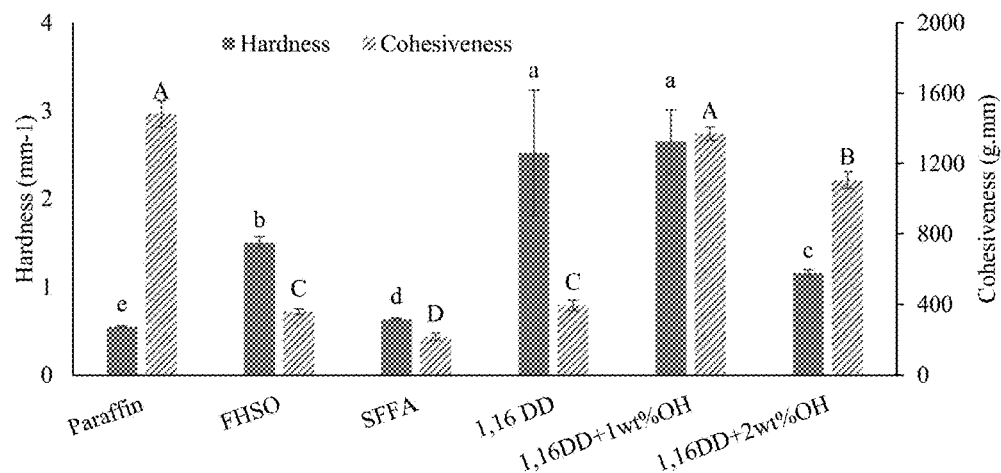
FIGS. 2A-2B compare the hardness and cohesiveness results of 1,16-hexadecanediol fatty acid diester (1,16 DD), 1,16 DD with various amounts of hydroxylated 1,16-hexadecanediol fatty acid diester (1,16 DD-OH) incorporated (i.e., 1,16 DD+1 wt % OH and 1,16 DD+2 wt % OH), ethylene glycol fatty acid diester (EGD), ethylene glycol fatty acid monoester/diester (EGMD), and EGMD with various amounts of hydroxylated ethylene glycol fatty acid diester (EGD-OH) incorporated (i.e., EGMD+0.5 wt % OH, EGMD+1 wt % OH, and EGMD+2 wt % OH), against the hardness and cohesiveness of the reference paraffin, the fully hydrogenated soybean oil (FHSO) and saturated free fatty acids (SFFA).

FIG. 2A showed that the incorporating 1,16 DD-OH into 1,16 DD led to a significantly improved cohesiveness for 1,16 DD. The mixture had an optimal hardness and cohesiveness when 1 wt % of —OH was introduced, while further increasing the amount of 1,16 DD-OH to a 2 wt % —OH in the mixture decreased both hardness and cohesiveness. The increase in cohesiveness was perhaps because the pendent hydroxyl group discouraged orderly packing and increased intermolecular interactions. The decrease of hardness was caused by the disorderly packing. It was observed that as the amount of 1,16 DD-OH increased, the mixture had a layer separation, possibly due to the structure difference between the two components. Such inhomogeneity of the mixture may have caused the reduction in cohesiveness.

Figure 2B:
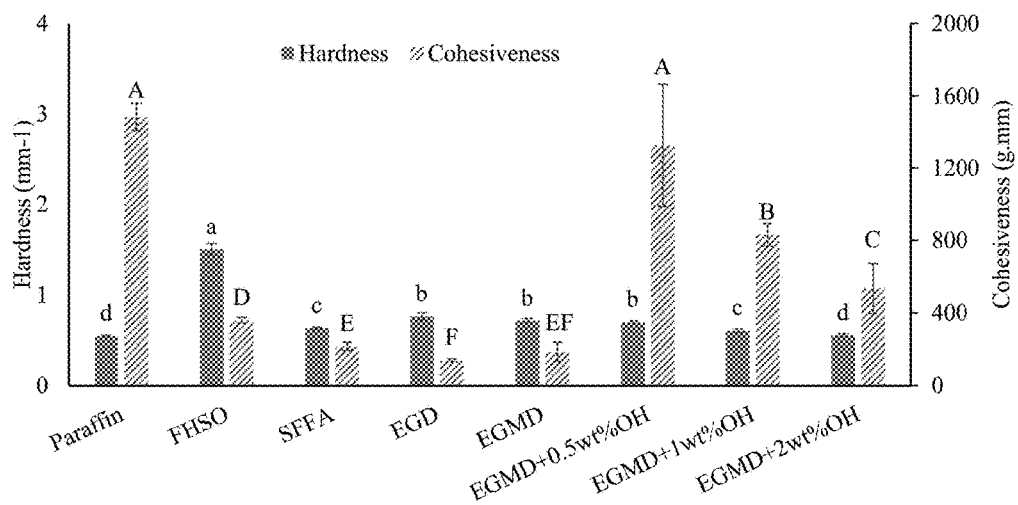

Because 1,16 diol is an expensive compound, the more affordable ethylene glycol was used as an alternative for the long-chain diol for the same chemistry. FIG. 2B shows that EGD and EGMD had a similar hardness and cohesiveness. However, EGMD was less powdery and had a better surface appearance than EGD. Therefore, EGMD was used for blending. When adding EGD-OH to EGMD, same trend as adding 1,16 DD-OH to 1,16 DD was observed. FIG. 2B shows that 0.5 wt % of —OH in the mixture resulted an optimal hardness and cohesiveness of the mixture. Similarly, the hardness and cohesiveness of this mixture also decreased when more pendent —OH was introduced, due to mixing difficulty. Previous studies also showed that incorporating hydroxyl groups and branch chains could improve intermolecular interactions which then significantly improved the cohesiveness of vegetable oil-based waxes (Feuge et al., "Modification of Vegetable Oils. XII. Plasticity of Some Aceto Derivatives of Monostearin," *J. Am. Oil Chem. Soc.* 29:11-14 (1952); U.S. Pat. No. 5,434,278 to Pelloso et al.; Wang et al., "Chemical Modification of Partially Hydrogenated Vegetable Oil to Improve its Functional Properties for Candles," *J. Am. Oil Chem. Soc.* 84:1149-59 (2007); Yao et al., "Textural and Physical Properties of Bio-Renewable 'Waxes' Containing Partial Acylglycerides," *J. Am. Oil Chem. Soc.* 89:155-66 (2012); and Yao et al., "Synthesis and Characterization of Acetylated and Stearylyzed Soy Wax," *J. Am. Oil Chem. Soc.* 90: 1063-71 (2013), which are herein incorporated by reference in their entirety). Comparing the long-chain diol derivatives, the EGMD matrix had a lower hardness. However, the hardness and cohesiveness of the EGMD+0.5 wt % pendent —OH product were very similar to that of paraffin.

Because EGMD+0.5 wt % OH had a hardness and cohesiveness comparable to that of paraffin, a more economical one-pot reaction process was designed to synthesize the mixture, as described in Example 3. The mixture was successfully synthesized and a one-pot reaction also eliminated the layer separation problem presented in mixing. However, the material produced by the one-pot reaction became slightly harder and less cohesive than the material produced by directly mixing the ester components. The average cohesiveness of the resulting material was about 1,000 g·mm compared to 1,300 g·mm of the material produced by mixing the ester components. This is possibly because the one-pot reaction resulted in randomization of monoester/diester compositions, which may lead to better molecular packing and compatibility.

Figure 3:
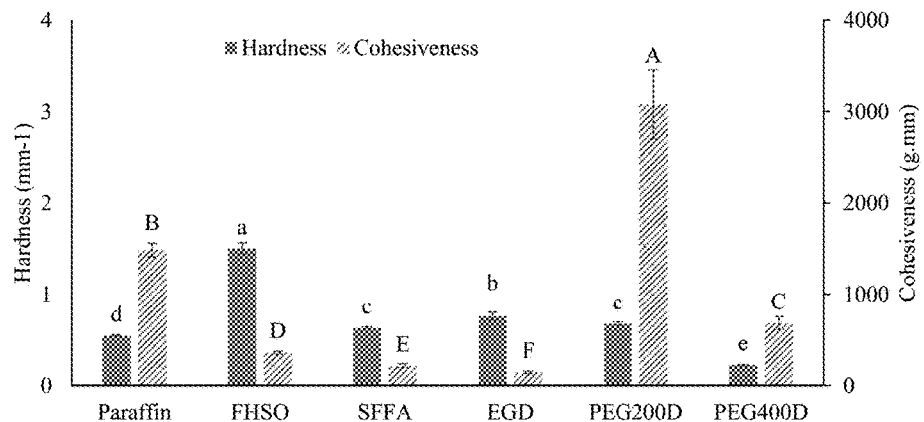
FIG. 3 compares the hardness and cohesiveness results of ethylene glycol fatty acid diester (EGD), PEG200 fatty acid diester (PEG200D), and PEG400 fatty acid diester (PEG400D), against the hardness and cohesiveness of the reference paraffin, the fully hydrogenated soybean oil (FHSO) and saturated free fatty acids (SFFA).

Diesters with C—O—C bond were also synthesized by reacting the SFFA with PEG200 (molecular weight of 200 g/mol) and PEG400 (molecular weight of 400 g/mol) at a molar ration of 2:1. FIG. 3 shows that PEG200D (PEG200 fatty acid diester) had a significantly higher cohesiveness than EGD and other materials, indicating C—O—C bond's tremendous impact on cohesiveness. However, C—O—C bond also negatively affected the hardness of the diester when the bond was in excess and, thus, PEG400D (PEG400 fatty acid diester) had a lowered hardness. A lower hardness also led to a lower measured cohesiveness since the material become less resistant to bending, though PEG400D would not crack after bending. The significant improvement in cohesiveness of PEG200D is probably due to the polyether part in the diester being flexible which provided the material with elasticity. Ether or ester bonds are attracted to each other via London forces and dipole-dipole interactions as well as chain entanglements, providing the material with elastic mechanical properties (Someya, Stretchable Electrons (Wiley-VCH, Weinheim, Germany, 2013), which is hereby incorporated by reference in its entirety).

Effect of Introducing a Ring Structure

Figure 4:
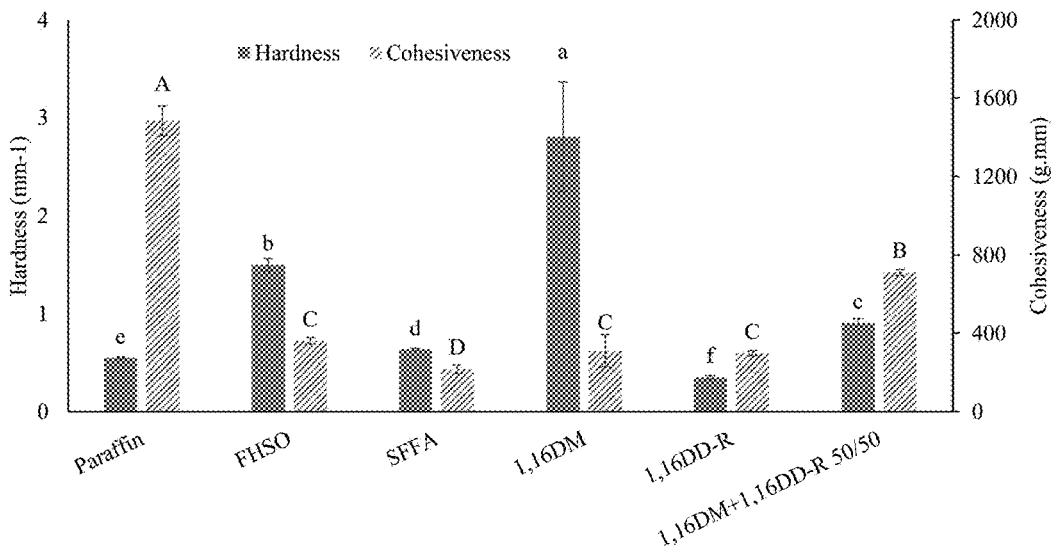
FIG. 4 compares the hardness and cohesiveness results of 1,16-hexadecanediol fatty acid monoester (1,16 DM), 1,16-hexadecanediol fatty acid and benzene diester (1,16 DD-R), and 1,16 DM blended with 1,16 DD-R at a ratio of 1:1 (i.e., 1,16 DM+1,16 DD-R (50/50)), against the hardness and cohesiveness of the reference paraffin, the fully hydrogenated soybean oil (FHSO) and saturated free fatty acids (SFFA).

The 1,16 DD-R compound was used to evaluate the effect of ring structure on the hardness and cohesiveness of the diester. FIG. 4 shows that attaching a benzene ring to the ester reduced the hardness. Such reduction in hardness is probably caused by the ring structure discouraging orderly packing of the molecules. Although benzene rings may serve as a hydrogen bonding acceptor and improve molecular interactions by promoting hydrogen bonding (Levitt et al., "Aromatic Rings Act as Hydrogen Bond Acceptors," *J. Mol. Biol.* 201: 751-54 (1988); Perutz, "The Role of Aromatic Rings as Hydrogen-Bond Acceptors in Molecular Recognition," *Phil Trans. R. Soc.* 345(1647): 105-112 (1993); Brinkley et al., "Hydrogen Bonding with Aromatic Rings," *AIChE Journal* 47(4): 948-53 (2001), which are hereby incorporated by reference in their entirety), cohesiveness was not improved in 1,16 DD-R since there was no hydrogen bond donor present. Blending 1,16 DM with 1,16 DD-R at a ratio of 1:1 to introduce a hydrogen bond donor resulted in a mixture with significantly improved cohesiveness (FIG. 4), which indicates that ring structures may improve cohesiveness by enhancing hydrogen bonding when hydrogen bond donors are present. However, the strength of such hydrogen bonding is weak, and the cohesiveness of the mixture is not comparable to that of paraffin.

Overall, PEG200D, EGMD+0.5 wt % OH, and 1,16 DD+1 wt % OH had a hardness and a cohesiveness comparable to that of paraffin, and were selected for further evaluations.

Water Repellency and Thermal Properties of the Selected Paraffin Substitutes

Since paraffin is mostly used as coating material, water repellency, melting profile, and coefficient of surface friction of the above selected three samples were determined.

Table 2 shows a comparison of physical properties of the three paraffin substitutes with the commercial paraffin used for coating as a benchmark. Table 2 shows that all three samples had similar melting peaks, while their water repellency values were different. Paraffin had the highest water contact angle while PEG200D had the lowest. The low contact angle of PEG200D was probably caused by the C—O—C group which is hydrogen bonding acceptor that can easily interact with water (Clayden et al., *Organic Chemistry* (1st Ed., Oxford University Press, U K, 2001), which is hereby incorporated by reference in its entirety). EGMD+0.5 wt % OH had a slightly higher water contact angle than 1,16DD+1 wt % OH, probably because of its lower content of pendent —OH group.

Because EGMD+0.5 wt % OH is more economical as it uses a less expensive ingredient, ethylene glycol, and has desirable properties, EGMD+0.5 wt % OH was further selected for evaluating coating performance and surface coefficient of friction analysis. The coating performance test was also conducted on PEG200D as a comparison.

TABLE 2

Physical Properties of the Exemplified Wax Composition in Comparison with the Reference Paraffin Wax

| Tests | PEG200D | 1,16DD + 1 wt % OH | EGMD + 0.5 wt % OH | Paraffin wax |
|---|---|---|---|---|
| | | Observation | | |
| Appearance | solid | solid | solid | solid |
| Color | semi-transparent to white | white | white | Clear, colorless to white |
| Hardness ($mm^{-1}$) | 0.68 ± 0.01 | 2.65 ± 0.37 | 0.69 ± 0.01 | 0.55 ± 0.01 |
| Cohesiveness (g · mm) | 3077 ± 379 | 1369 ± 39 | 1325 ± 338 | 1484 ± 75 |
| Melting Peak | 71 ± 2° C. | 67 ± 4° C. | 65 ± 3° C. | 67 ± 2° C. |
| Solubility in water (@ 23° C.) | Insoluble | Insoluble | Insoluble | Insoluble |
| Surface Water Contact Angle | 65 ± 5° | 85 ± 2° | 92 ± 4° | 103 ± 2° |

Table 3 shows that PEG200D had a significantly higher wax adsorption rate, which resulted in the highest cardboard strength, compared to that of paraffin and EGD-OH-0.5 wt %. The adsorption rates of paraffin and EGD-OH had no significant difference, and the resulting cardboard had similar strength.

TABLE 3

Adsorption Rate of Waxes and Strength of the Coated Cardboard

| | Paraffin | PEG200D | EGMD-0.5 wt % OH |
|---|---|---|---|
| Wax adsorption (wt %) | 49.0 ± 1.0$^B$ | 53.6 ± 0.6$^A$ | 48.8 ± 2.4$^B$ |
| Cardboard Strength (g) | 12730 ± 508$^b$ | 15475 ± 386$^a$ | 13233 ± 2748$^{ab}$ |

Overall, PEG200D and EGMD+0.5 wt % OH were very comparable to paraffin regarding contributing weight and strength to the cardboard.

Example 8—Additional Characterization of Synthesized Soybean Oil-Based Waxes

The wax samples synthesized in Examples 1-4 were further characterized and tested.

a. Observation of Wax Crystallization Using Polarized Light Microscopy

To determine how the chemical structures of the waxes qualitatively affect the crystal structures and consequently the physical properties, the microstructures of selected waxes were observed using Polarized Light Microscopy (PLM).

Samples were prepared following the method reported by Wang et al., "Chemical Modification of Partially Hydrogenated Vegetable Oil to Improve its Functional Properties for Candles," *J. Am. Oil Chem. Soc.* 84:1149-59 (2007), which is herein incorporated by reference in its entirety, with minor modifications. Briefly, a small amount of a wax sample was loaded on the glass microscopy slides and heated in an oven at 5° C. above the melting temperature of the wax for 30 minutes. A preheated cover slide was then slipped over the molten wax to produce a thin film. The prepared slide was cooled at room temperature for one hour and then analyzed with a DIC microscope (Olympus BX53, Olympus Corporation, MA, USA) using CellSens Dimension software (Olympus Corporation, MA, USA). The crystal pictures for the wax samples were taken at 100× magnification.

b. Coating Performance Tests of the Selected Waxes

The wax synthesized in Examples 1-4 which had similar hardness, cohesiveness, and melting points as those of paraffin were selected for simulated coating performance tests.

To prepare coated cardboard samples, non-coated corrugated cardboard was cut into approximately 50 mm×50 mm pieces and submerged into molten waxes for 10 seconds. These coated cardboard pieces were left to solidify for 3 hours at room temperature, and excessive wax was allowed to drain from the cardboard along the flute vertically. The wax absorption rates of the wax-coated cardboard samples were calculated relative to the original cardboard weight without wax coated using the following equation:

$$\text{Wax absorption (\%)} = \frac{(\text{Weight with wax} - \text{Weight without wax})}{\text{Weight with wax}} \times 100$$

The strengths of the coated cardboards were evaluated using a bending test. The cardboard sample were placed on two vertical support bars that were 14 mm apart and a blade attached to the crosshead of the instrument was driven perpendicular into the sample at a speed of 1 mm/second, with 10 mm of travel distance. The peak bending force was considered as the cardboard strength.

Ice-water soaking tests were conducted on the coated cardboards to evaluate water resistance of the coated cardboards. Samples were soaked in ice water for 24 hours and water in the wet cardboard was allowed to drain for 5 minutes. The same bending test discussed above was used to evaluate the effect of soaking on the cardboard strength. Another water resistance test was also conducted, to determine the strengths of the coated cardboards before and after the surface wetting. Water (4 drops) was applied to the surface of the coated cardboard and allowed to penetrate for 2 hours. The wet surface that had a larger area than the probe was tested. A 3 mm stainless steel probe was used to penetrate the surface for 2 mm at a speed of 0.5 mm/second, and the peak force was recorded as the strength of the wet surface.

The effect of hydrophobic particles on the coating performance and water resistance of the cardboards was also tested. A hydrophobic silica nanoparticle product (6864HN, 10-25 nm) was purchased from SkySpring Nanomaterials, Inc. (Houston, Tex., USA), and a hydrophobic silica microparticle (Dumacil 300FGK, 15 μm) product was provided by Elementis Specialties (East Windsor, N.J., USA).

Hydrophobic nanoparticles (6864HN) and microparticles (Dumacil 300FGK) were mixed at concentrations of 1, 5, and 10 wt % with selected waxes using a homogenizer. The effect of substituting a portion of paraffin with the oil-based wax was evaluated at 30% and 50% substitution. PEG200D (or EGMD+0.5 wt % OH) and paraffin were weighed into a beaker at weight ratios of 3:7 and 1:1 for 30% and 50% substitution, respectively. The oil-based wax/paraffin blend was heated at 80° C. for 5 minutes with continuous mixing using a magnetic stir until a homogeneous liquid was obtained.

Cardboard samples coated with the wax/paraffin blends were prepared and tested for the ice-water soaking test and surface wetting and penetration test. The strength of the cardboard before and after soaking or wetting was measured using the same settings as discussed above.

Washability of the selected waxes from the coated cardboard samples was determined following the standard repulpability test procedure (the Corrugated Packaging Alliance protocol, 2010) with minor modifications. Coated cardboard samples were cut into about 50 mm×50 mm pieces and the initial weights of these samples were recorded. Each sample was placed in 1,000 mL of boiling water in a one-gallon Waring blender (New Brunswick Scientific Supply Co., Inc., Edison, N.J.) and then blended on low speed for 1 minute. The fibers and particles were still large after blending and unable to pass through a sieve with 0.01 inch opening. All fibers along with wax residues were rinsed out of the blender onto the sieve and then the mass on the screen was washed with hot tap water (52±5° C.) for 3 minutes. The material that remained on top of the sieve was collected and dried in an oven at 105° C. for 12 hours. The dry weight of the fiber and particles was obtained and percentage of the wax washed off was calculated using the following equation:

$$\% \text{ of wax washable} = \frac{(\text{Initial weight} - \text{weight of remainder})}{\text{Initial weight} \times \% \text{ wax absorbed}} \times 100$$

Discussion of Examples 8a-8b

Water Repellency, Thermal Properties, and Coating Performance

Table 2 shown in Discussion of Examples 1-7 above illustrates the comparison of physical properties for the three paraffin substitutes with a commercial paraffin product as a benchmark. As discussed in that section, EGMD+0.5 wt % OH was selected for coating performance evaluation and surface coefficient of friction analysis. Coating performance testing was also conducted for PEG200D as a comparison.

Table 4 shows that PEG200D had a significantly higher wax absorption, which resulted in the highest cardboard strength, compared to that of paraffin and EGMD+0.5 wt % OH. The absorption rate of paraffin and EGMD+0.5 wt % OH had no significant difference, and the resulting cardboards had similar strength.

TABLE 4

Comparison of coating performance of selected waxes and effect of nanoparticles

| | Wax absorption (%) | Wax washable (%) | Water absorption (%) | Strength before soaking (g) | Strength after soaking (g) | Strength reduction after soaking (%) |
|---|---|---|---|---|---|---|
| Paraffin | 49.2 ± 2.7 $^E$ | 33.9 ± 3.3 $^D$ | 15.3 ± 3.2 $^F$ | 12,867 ± 496 $^C$ | 2,888 ± 362 $^{BCD}$ | 77.4 ± 3.7 $^B$ |
| PEG200D | 53.8 ± 0.6 $^{CD}$ | 90.0 ± 2.5 $^A$ | 43.1 ± 1.3 $^B$ | 15,475 ± 386 $^{BC}$ | 1,976 ± 129 $^{CD}$ | 87.2 ± 0.7 $^{AB}$ |
| EGMD 0.5 wt % OH | 49.1 ± 2.0 $^E$ | 85.5 ± 0.7 $^B$ | 51.2 ± 1.4 $^A$ | 13,233 ± 2,748 $^C$ | 1,404 ± 14 $^D$ | 89.1 ± 2.0 $^A$ |
| PEG200D 1 wt % Nanoparticle | 52.2 ± 2.8 $^{DE}$ | — | 34.3 ± 2.8 $^C$ | 13,749 ± 1,022 $^C$ | 2,709 ± 268 $^{BCD}$ | 80.1 ± 3.5 $^{AB}$ |
| PEG2000 5 wt % Nanoparticle | 57.5 ± 3.2 $^{BC}$ | — | 29.1 ± 2.5 $^D$ | 15,842 ± 1,800 $^{BC}$ | 3,537 ± 352 $^{BC}$ | 77.6 ± 0.6 $^{AB}$ |
| PEG200D 10 wt % Nanoparticle | 61.2 ± 1.4 $^{AB}$ | 91.1 ± 1.0 $^A$ | 25.1 ± 1.3 $^{DE}$ | 18,771 ± 860 $^{AB}$ | 3,854 ± 752 $^B$ | 79.4 ± 4.1 $^{AB}$ |
| EGMD + 0.5 wt % OH 1 wt % Nanoparticle | 48.9 ± 1.7 $^E$ | — | 34.6 ± 3.3 $^C$ | 13,553 ± 1,230 $^C$ | 2,144 ± 362 $^{BCD}$ | 83.9 ± 4.1 $^{AB}$ |
| EGMD + 0.5 wt % OH 5 wt % Nanoparticle | 53.6 ± 0.8 $^C$ | — | 28.2 ± 1.0 $^{DE}$ | 13,792 ± 2540 $^C$ | 3,167 ± 352 $^{BC}$ | 76.2 ± 6.5 $^B$ |
| EGMD ± 0.5 wt % OH 10 wt % Nanoparticle | 62.4 ± 2.7 $^A$ | 77.1 ± 0.4 $^C$ | 23.4 ± 6.1 $^E$ | 21,585 ± 4,033 $^A$ | 7,457 ± 2973 $^A$ | 63.3 ± 19.0 $^C$ |

In each column, means with the same letters are not significantly different at p = 0.05.

The water resistance of the wax-coated cardboard was determined by soaking in ice water for 24 hours and the strength of the cardboard was measured. Table 4 shows that neither PEG200D nor EGMD+0.5 wt % OH had comparable water resistance to paraffin. The ether groups in PEG200D and hydroxyl groups in EGMD+0.5 wt % OH led to a high degree of water penetration.

However, both PEG200D and EGMD+0.5 wt % OH had a significantly higher ability to be dispersed and washed away by water compared to paraffin. About 90% of PEG200D and 85% of EGMD+0.5 wt % OH coated on the cardboard samples could be removed by blending in hot water.

Furthermore, the water resistance of PEG200D and EGMD+0.5 wt % OH could be improved with the addition of hydrophobic nanoparticles, as shown in Table 4. The addition of 5 wt % of hydrophobic nanoparticles to PEG200D and EGMD+0.5 wt % OH resulted in a strength comparable to the paraffin-coated cardboard after soaking. Additionally, the use of hydrophobic particles did not significantly reduce the quantity of washable wax. This is because that the hydrophobic nanoparticles may have blocked the surface pores that water can access, or have interacted with the wax components, leading to a significantly lowered water binding.

A more affordable hydrophobic microparticle product was used to mix with the wax samples to improve the water resistance. The effect of partial substitution of paraffin with PEG200D and EGMD+0.5 wt % OH on the water resistance was also evaluated.

Table 5 shows that 30 wt % and 50 wt % substitution of paraffin with PEG200D and EGMD+0.5 wt % OH resulted in a lower or similar bending strength reduction after soaking, as compared to paraffin, which indicated that the two materials could substitute up to 50% of paraffin without losing the desirable functionalities. With PEG200D and EGMD+0.5 wt % OH being relatively more hydrophilic than paraffin, the mixtures also had significantly higher washability than paraffin. For surface penetration strength test after wetting, the partial substitution of paraffin resulted in a higher strength reduction.

The addition of the hydrophobic microparticles to PEG200D did not improve its water resistance, whereas significant improvement was achieved when the hydrophobic microparticles were added to EGMD+0.5 wt % OH. When adding 5 wt % microparticles to EGMD+0.5 wt % OH, the bending strength after soaking and the surface penetration strength after wetting of the coated cardboard samples showed no significant difference from those coated with paraffin. Furthermore, the washability of EGMS+0.5 wt % OH with microparticles added was significantly higher than that of paraffin.

TABLE 5

Comparison of coating performance for waxes mixed with paraffin and silica microparticles

| | Wax absorption (%) | Wax washable (%) | Water absorption (%) | Strength before soaking (g) | Penetration strength before wetting (g) | Strength reduction after soaking (%) | Penetration strength reduction after wetting (%) |
|---|---|---|---|---|---|---|---|
| Paraffin | 49.2 ± 0.9 $^{CD}$ | 34.0 ± 4.1 $^E$ | 15.3 ± 3.2 $^E$ | 12,867 ± 496 $^{BC}$ | 3,623 ± 555 $^{BC}$ | 77.4 ± 3.7 $^{BC}$ | 15.9 ± 0.8 $^F$ |
| Paraffin 30 wt % PEG200D | 48.1 ± 1.3 $^{DE}$ | 91.5 ± 1.3 $^{AB}$ | 30.9 ± 0.3 $^A$ | 11,308 ± 1,718 $^{DE}$ | 4,244 ± 395 $^A$ | 81.0 ± 1.7 $^B$ | 42.5 ± 7.5 $^C$ |
| Paraffin 50 wt % PEG200D | 50.6 ± 0.8 $^{BC}$ | 93.4 ± 1.0 $^A$ | 29.1 ± 1.0 $^A$ | 10,911 ± 992 $^E$ | 3,701 ± 523 $^{ABC}$ | 75.7 ± 1.4 $^{BCD}$ | 32.4 ± 6.6 $^{DE}$ |

TABLE 5-continued

Comparison of coating performance for waxes mixed with paraffin and silica microparticles

| | Wax absorption (%) | Wax washable (%) | Water absorption (%) | Strength before soaking (g) | Penetration strength before wetting (g) | Strength reduction after soaking (%) | Penetration strength reduction after wetting (%) |
|---|---|---|---|---|---|---|---|
| Paraffin 30 wt % EGMD-0.5 wt % OH | 47.2 ± 1.5 $^E$ | 83 ± 1.7 $^C$ | 17.1 ± 0.9 $^{DE}$ | 12,676 ± 708 $^{BCD}$ | 3,897 ± 362 $^{AB}$ | 70.4 ± 4.1 $^D$ | 43.1 ± 2.8 $^C$ |
| Paraffin 50 wt % EGMD-0.5 wt % OH | 51.3 ± 0.7 $^B$ | 86.7 ± 1.9 $^{BC}$ | 14.1 ± 3.3 $^{EF}$ | 12,489 ± 431 $^{BCD}$ | 3,488 ± 138 $^{BC}$ | 75.4 ± 1.9 $^{BCD}$ | 45.8 ± 0.4 $^C$ |
| PEG200D 1 wt % Microparticle | 51.8 ± 0.8 $^B$ | — | 31.8 ± 1.1 $^A$ | 11,685 ± 181 $^{CDE}$ | 3,308 ± 452 $^{BC}$ | 91.6 ± 0.4 $^A$ | 79.4 ± 3.3 $^A$ |
| PEG200D 5 wt % Microparticle | 61.4 ± 0.1 $^A$ | — | 21.3 ± 1.5 $^{BC}$ | 13,593 ± 242 $^B$ | 3,236 ± 389 $^C$ | 90.8 ± 1.0 $^A$ | 76.0 ± 1.7 $^A$ |
| PEG200D 10 wt % Microparticle | 61.9 ± 0.3 $^A$ | 86.2 ± 0.8 $^{BC}$ | 24.3 ± 2.7 $^B$ | 13,192 ± 1,606 $^{BC}$ | 3,285 ± 28 $^C$ | 88.8 ± 2.8 $^A$ | 64.9 ± 3.2 $^B$ |
| EGMD-0.5 wt % OH 1 wt % Microparticle | 51.6 ± 0.2 $^D$ | — | 19.3 ± 0.2 $^{CD}$ | 13,485 ± 310 $^{BC}$ | 4,231 ± 383 $^A$ | 74.8 ± 8.2 $^{BCD}$ | 35.1 ± 6.1 $^D$ |
| EGMD-0.5 wt % OH 5 wt % Microparticle | 50.1 ± 2.1 $^{BC}$ | — | 18.0 ± 2.3 $^{CDE}$ | 15,594 ± 156 $^A$ | 3,793 ± 343 $^{ABC}$ | 72.4 ± 2.3 $^{CD}$ | 13.0 ± 2.0 $^F$ |
| EGMD-0.5 wt % OH 10 wt % Microparticle | 60.9 ± 0.5 $^A$ | 75.5 ± 0.9 $^D$ | 11.4 ± 1.3 $^F$ | 15,974 ± 249 $^A$ | 3,529 ± 73 $^{BC}$ | 74.4 ± 7.2 $^{BCD}$ | 25.6 ± 0.7 $^E$ |

In each column, means with the same letters are not significantly different at p = 0.05.

Figure 5:
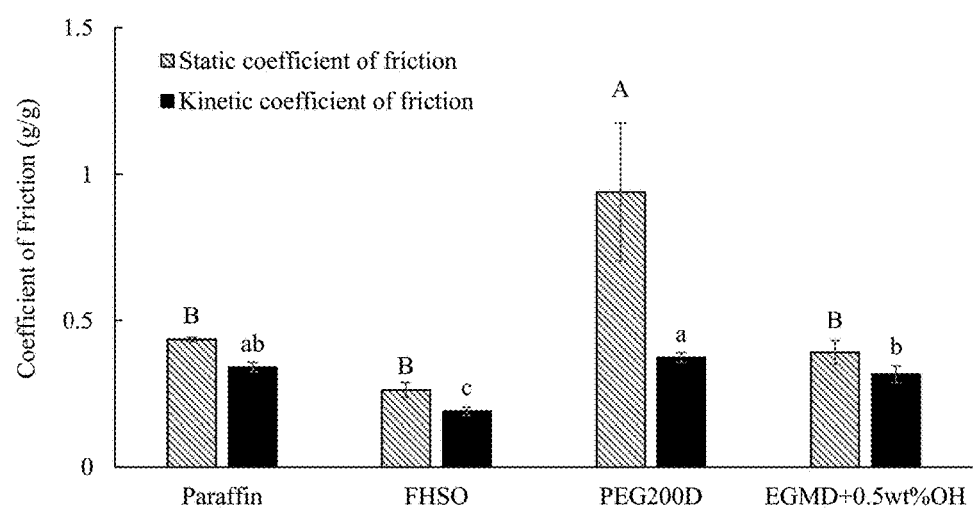
FIG. 5 compares the coefficient of friction results of PEG200 fatty acid diester (PEG200D) and ethylene glycol fatty acid monoester/diester (EGMD) with 0.5 wt % hydroxylated ethylene glycol fatty acid diester (EGD-OH) incorporated (i.e., EGMD+0.5 wt % OH), against the coefficient of friction results of the reference paraffin and the fully hydrogenated soybean oil (FHSO). Means with the same letters are not significantly different at p=0.05.

The surface coefficient of friction for wax-coated surfaces was also measured. FIG. 5 shows that PEG200D had a higher static and kinetic coefficients of friction compared to other samples, but its kinetic coefficient of friction was not significantly different from that of paraffin. EMGD+0.5 wt % OH had static and kinetic coefficients of friction very similar to those of paraffin.

Morphology of Wax Crystalline

Figure 6:
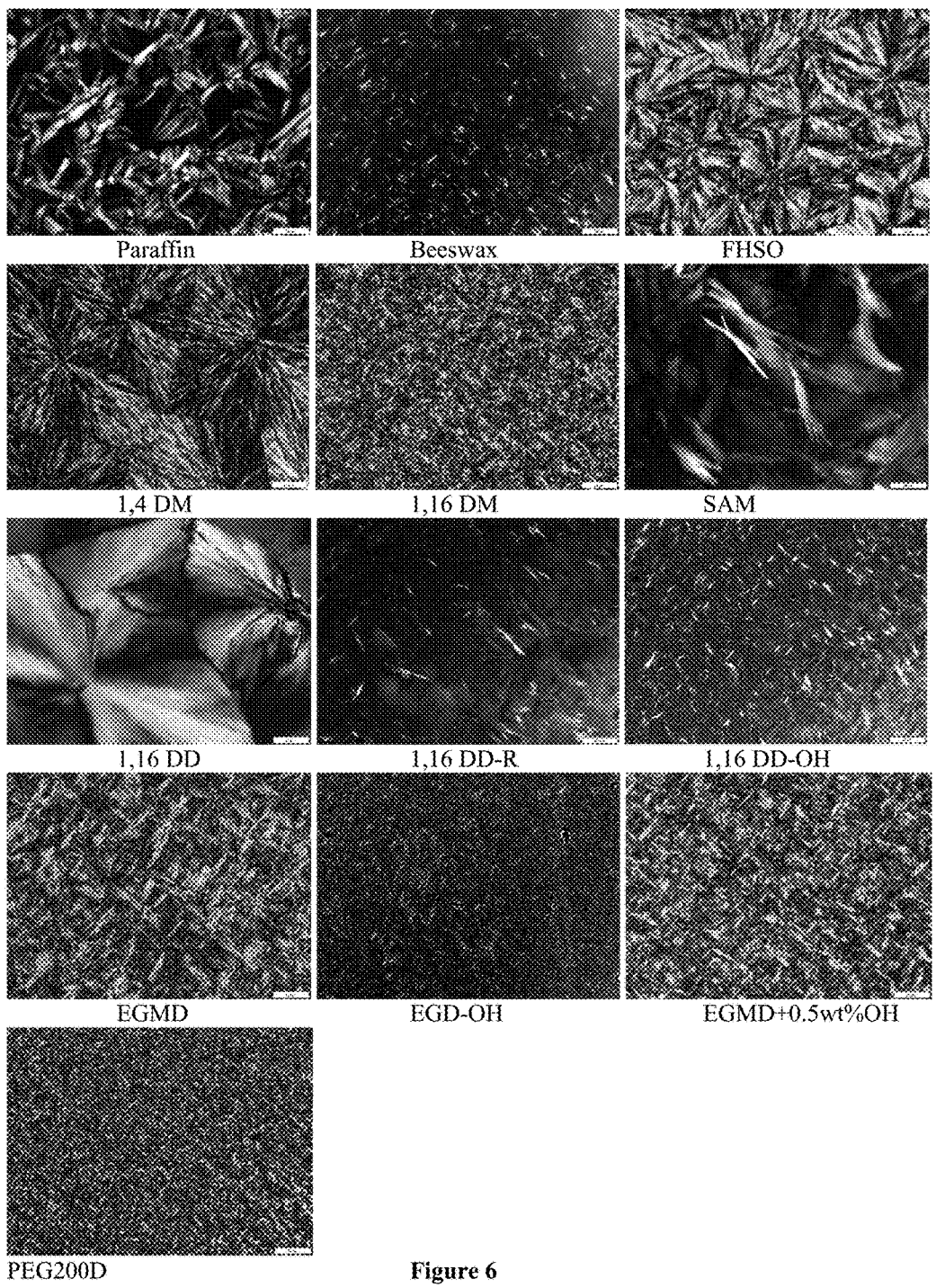
FIG. 6 are pictures showing the crystal morphology of selected waxes (paraffin; beeswax; FHSO—the fully hydrogenated soybean oil; 1,4 DM—1,4-butanediol fatty acid monoester; 1,16 DM—1,16-hexadecanediol fatty acid monoester; SAM—stearyl alcohol fatty acid monoester; 1,16 DD—1,16-hexadecanediol fatty acid diester; 1,16 DD-R—1,16-hexadecanediol fatty acid and benzene diester; 1,16 DD-OH—hydroxylated 1,16-hexadecanediol fatty acid diester; EGMD—ethylene glycol fatty acid monoester/diester; EGD-OH—hydroxylated ethylene glycol fatty acid diester; and EGMD+0.5 wt % OH—EGMD with 0.5 wt % EGD-OH incorporated) at 100× magnification at 23° C. White bar in lower right corner indicates 20 μm.

FIG. 6 shows the crystal morphology of selected waxes at 23° C. after 1 hour of stabilization at room temperature. Paraffin, beeswax, 1,16 DD-R, 1,16 DD-OH, and EGD-OH all showed needle-like crystals, although their sizes and networks were different. Unlike paraffin wax, which had dendritic crystals forming junction points, beeswax, 1,16 DD-R, 1,16 DD-OH, and EGD-OH all had much finer crystals. This may be because that the needle crystals allowed more contacts among the microstructural elements and possibly contributed to the good cohesiveness of these waxes, which may have explained the increased cohesiveness when 1,16 DD-R, 1,16 DD-OH and EGD-OH were added to 1,16 DM, 1,16DD, and EGMD, respectively. The EGMD+0.5 wt % OH, as compared to EGMD, had similar crystal shape, except finer and tighter packing; and very much like paraffin, the crystalline structure of EGMD+0.5 wt % OH was highly interconnected, which may have contributed to its improved cohesiveness. Crystals of 1,16 DM and PEG200D were less needle-like but highly interconnected, and 1,16 DM had larger crystals than PEG200D. It is possible for 1,16 DM molecules with a hydroxyl group at the terminal position to interact and form larger crystals via hydrogen bonding. While PEG200D molecules probably interacted with each other in a very different way, leading to a hardness and cohesiveness very different from that of 1,16 DM. FHSO, 1,4 DM, and 1,16 DD crystallized into more ordered and larger crystals. The ordered crystalline state may have contributed to a high hardness, but a negatively affected cohesiveness. The PLM results showed that the physical properties of these wax samples may be explained by their crystal morphology.

Example 9—Evaluation of Antimicrobial Effect of Synthesized Soybean Oil-Based Waxes The wax samples synthesized in Examples 1-4 were used to prepare coating compositions and tested for antimicrobial effect.

*Listeria monocytogenes* and *Salmonalle enteritidis* were used for screening the antimicrobial effect of the wax coatings, and brain heart infusion (BHI) broth and phosphate buffer solution (PBS) were used for sample preparation. Soybean oil was used as a control, hydroxylated ethylene glycol fatty acid diester (EGD-OH), and PEG400 fatty acid diester (PEG400D) were tested as wax samples. EGD-OH was prepared according to the methods illustrated in Examples 1-3 and PEG400D was prepared according to the methods illustrated in Examples 1-3 and Scheme 11.

For fat emulsion preparation, Tween 80 (Polysorbate 80) emulsifier was dissolved in PBS solution at a concentration of 0.5%. Five grams of the two wax samples were each added to 100 mL of the PBS-emulsifier solution and blended for 2 minutes, to create the stock wax emulsions. The EGD-OH sample was fully dispersible, while the dispersibility of the PEG400D sample was 3.387 mg/mL, due to its high melting temperature. These wax emulsions in various quantities were added to the BHI broth to create three wax concentration levels for microbial growth test.

The bacterial dispersions of 30-μL aliquots with cell concentration of $10^7$ CFU/mL were added to 3-mL portions of BHI broth containing different concentrations of the wax emulsions. Aliquots (250 μL each) of the inoculated broth were transferred to a 100-well plate and incubated at 37° C. in the Bioscreen C turbidometer for 24 hours. The absorbance (at 600 nm) of the broth were recorded every 30 min. For each of the following treatments, three samples were prepared:

Negative control 1 (NC 1): BHI broth only;
Negative control 2 (NC 2): BHI broth+PBS-emulsifier solution;
Negative control 3 (NC 3): BHI broth+wax emulsion;
Positive control 1 (PC 1): BHI broth+bacteria;
Positive control 2 (PC 2): BHI broth+bacteria+PBS-emulsifier solution;
Treatment 3 (T3): BHI broth+bacteria+wax emulsion;

The bacterial inhibition effect of the wax emulsion is calculated using the following equation:

$$\text{Inhibition effect (\%)} = \frac{OD(PBS-\text{emulsifier solution}) - OD(\text{wax emulsion})}{OD(PBS-\text{emulsifier solution})}$$

In the above equation, OD (PBS-emulsifier solution) is the optical density at 600 nm for the PBS-emulsifier solution control at 24 hours, calculated by the difference in the absorbance between PC2 and NC2. The values for PC2 and NC2 were the means from three measurements. OD (wax emulsion) is the optical density at 600 nm for the wax emulsion treatment at 24 hours, calculated by the difference in the absorbance between T3 and NC3. The values for T3 and NC3 were means from three measurements.

The results are listed in Table 6. As shown in Table 6, both coating materials (the two wax emulsion samples) had strong antimicrobial effect, and the effect was dose dependent, indicating that the coating compositions prepared from the soybean oil-based waxes had antimicrobial effect on food-borne pathogens.

What is claimed:

1. A process for preparing a wax composition, comprising:
providing one or more saturated free fatty acids having the formula of

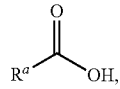

wherein $R^a$ is a substituted or unsubstituted $C_4$ to $C_{50}$ alkyl;
providing a polyethylene glycol having the formula of

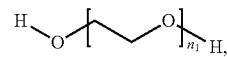

a diol having a formula of

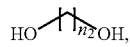

or mixture thereof, wherein $n_1$ is an integer from 2 to 10, and $n_2$ is an integer from 2 to 24;
reacting the polyethylene glycol, the diol, or mixture thereof with the one or more saturated free fatty acids in the presence of an esterification catalyst at a temperature of 60° C. to 120° C., to form one or more fatty acid monoester or diester compounds; and
removing the esterification catalyst from the formed fatty acid monoester or diester compounds.

2. The process of claim 1, wherein the esterification catalyst is a strong acidic ion exchange resin.

3. The process of claim 1, wherein the one or more saturated free fatty acids are prepared from a fully hydrogenated vegetable oil.

4. The process of claim 3, wherein the fully hydrogenated vegetable oil is fully hydrogenated soybean oil, fully hydrogenated cottonseed oil, fully hydrogenated sunflower oil,

TABLE 6

Effect of lipid type and concentration on degree of growth inhibition (%) of the two food pathogens tested.

| | Wax emulsion and its concentration | | | | | | | | |
|---|---|---|---|---|---|---|---|---|---|
| | SO, 1 mg/mL | SO, 10 mg/mL | SO, 15 mg/mL | EGD, 1 mg/mL | EGD, 10 mg/mL | EGD, 15 mg/mL | PEG, 0.07 mg/mL | PEG, 0.7 mg/mL | PEG, 1.0 mg/mL |
| Salmonella Enteritidis | 5.7 | 35.0 | 38.7 | 14.7 | 115.6 | 134.7 | 37.1 | 77.2 | 82.3 |
| Listeria monocytogenes | 6.9 | 16.8 | 22.5 | 13.5 | 97.8 | 106.0 | 8.7 | 89.3 | 96.8 |

SO = soybean oil emulsion; EGD = emulsion of EGD—OH; PEG = PEG400D emulsion.
Inhibition percentage >100% is due to the clarity of the growth well was better than that of the control.

Although preferred embodiments have been depicted and described in detail herein, it will be apparent to those skilled in the relevant art that various modifications, additions, substitutions, and the like can be made without departing from the spirit of the present invention and these are therefore considered to be within the scope of the present invention as defined in the claims which follow.

fully hydrogenated canola oil, fully hydrogenated corn oil, fully hydrogenated palm oil, fully hydrogenated olive oil, fully hydrogenated peanut oil, fully hydrogenated safflower oil, fully hydrogenated coconut oil, fully hydrogenated rapeseed oil, fully hydrogenated castor oil, fully hydrogenated mustardseed oil, or a mixture thereof.

5. The process of claim 4, wherein the fully hydrogenated vegetable oil is fully hydrogenated soybean oil.

6. The process of claim 1, wherein the molar ratio of the polyethylene glycol, the diol, or mixture thereof to the one or more saturated free fatty acid ranges from 1:1 to 1:2.

7. The process of claim 1 further comprising:
blending the formed fatty acid monoester or diester compounds with one or more hydroxylated fatty acid diester compounds.

8. The process of claim 7, wherein the one or more hydroxylated fatty acid diester compounds are prepared by the process comprising:
providing a hydroxylated free fatty acid having the formula of

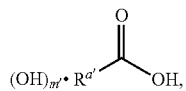

wherein $R^{a'}$ is a substituted or unsubstituted $C_4$ to $C_{50}$ alkyl, m' is an integer from 1 to 6, and $.(OH)_{m'}$ represents 1 to 6 hydroxyl groups substituting for 1 to 6 hydrogen atoms in the alkyl group $R^{a'}$;

providing a polyethylene glycol having the formula of

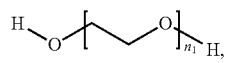

a diol having a formula of

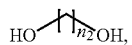

or mixture thereof, wherein $n_1$ is an integer from 2 to 10, and $n_2$ is an integer from 2 to 24;

reacting the polyethylene glycol, the diol, or mixture thereof, with the hydroxylated free fatty acid in the presence of an esterification catalyst at a temperature of 60° C. to 120° C., to form one or more hydroxylated fatty acid diester compounds; and removing the esterification catalyst from the formed hydroxylated fatty acid monoester or diester compounds.

9. The process of claim 8, wherein the esterification catalyst is a strong acidic ion exchange resin.

10. The process of claim 8, wherein the hydroxylated free fatty acid is prepared by oxidizing-hydrolyzing an epoxidized free fatty acid.

11. The process of claim 8, wherein the molar ratio of the polyethylene glycol, the diol, or mixture thereof to the hydroxylated free fatty acid ranges from 1:1 to 1:2.

* * * * *